(12) United States Patent
Cai et al.

(10) Patent No.: US 8,426,419 B2
(45) Date of Patent: *Apr. 23, 2013

(54) TYROSINE KINASE INHIBITORS CONTAINING A ZINC BINDING MOIETY

(75) Inventors: Xiong Cai, Bedford, MA (US); Changgeng Qian, Wayland, MA (US); Stephen Gould, San Carlos, CA (US); Haixiao Zhai, Bedford, MA (US)

(73) Assignee: Curis, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/010,542

(22) Filed: Jan. 20, 2011

(65) Prior Publication Data

US 2011/0178095 A1    Jul. 21, 2011

Related U.S. Application Data

(62) Division of application No. 11/852,450, filed on Sep. 10, 2007, now Pat. No. 7,888,361.

(60) Provisional application No. 60/843,730, filed on Sep. 11, 2006, provisional application No. 60/895,901, filed on Mar. 20, 2007.

(51) Int. Cl.
*A61K 31/506* (2006.01)
*C07D 403/12* (2006.01)

(52) U.S. Cl.
USPC ...... 514/252.19; 514/256; 514/269; 544/319; 544/328

(58) Field of Classification Search ............ 514/252.19, 514/256, 269; 544/319, 328
See application file for complete search history.

(56) References Cited

U.S. PATENT DOCUMENTS

2004/0054186 A1    3/2004 Das et al.

FOREIGN PATENT DOCUMENTS

| JP | 2003-528074 A | 9/2003 |
|---|---|---|
| JP | 2006-523216 A | 10/2006 |
| WO | 01/70675 A2 | 9/2001 |
| WO | 2004/085388 A2 | 10/2004 |
| WO | 2005/077945 A2 | 8/2005 |
| WO | 2006/016680 A1 | 2/2006 |
| WO | WO 2006/037032 A2 | 4/2006 |
| WO | WO 2006/081172 A2 | 8/2006 |

OTHER PUBLICATIONS

Takai et al., PubMed Abstract (Cancer 101(12):2760-70), Dec. 2004.*
Glaser, HDAC inhibitors: Clinical update and mechanism-based potential, Biochemical Pharmacology, 74, pp. 659-671, 2007.*
Simone, Oncology: Introduction, Cecil Textbook of Medicine, 20th Edition, vol. 1, pp. 1004-1010, 1996.*
Traxler, Protein Tyrosine Kinase inhibitors in cancer treatment, Expert Opinion on Therapeutic Patents, 7(6): 571-588, 1997.*
Cressey et al., Medline Abstract (BMC Cancer , vol. 5, p. 128) Oct. 2005.*
Fabbro et al., Protein Kinases as targets for anticancer agents: from inhibitors to useful drugs, Pharmacology & Therapeutics 93 (2002) 79-88.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Damasio, Alzheimer's Disease and Related Dementias, Cecil Textbook of Medicine, 20th Edition, vol. 2, pp. 1992-1996 (1996).*
Layzer, Degenerative Diseases of the Nervous System, Cecil Textbook of Medicine, 20th Edition, vol. 2, pp. 2050-2057 (1996).*
West, Solid Solutions, Solid State Chemistry and its applications, Wiley, New York, pp. 358 and 361, 1988.*
Vippagunta et al., Crystalline solids, Advanced Drug Delivery Reviews, 48 (2001), pp. 3-26, 2001.*
Ulrich, Crystallization, Kirk-Othmer Encyclopedia of Chemical Technology, vol. 8, pp. 113-120, Aug. 2002.*
Lombardo, L. J., et al., "Discovery of N-(2-Chloro-6-methylphenyl)-2-(6-(4-(2-hydroxyethyl)-piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays," J. Med. Chem., 47(27): 6658-6661 (2004).
Chen, P., et al., "Discovery of novel 2-(aminoheteroaryl)-thiazole-5-carboxamides as potent and orally active Src-family kinase $p$ 56$^{Lck}$ inhibitors," Bioorganic & Medicinal Chemistry Letters, 14: 6061-6066 (2004).

* cited by examiner

*Primary Examiner* — Deepak Rao
(74) *Attorney, Agent, or Firm* — Elmore Patent Law Group, P.C.; Edgar W. Harlan; Carolyn S. Elmore, Esq.

(57) ABSTRACT

The present invention relates to tyrosine kinase inhibitors that contain a zinc-binding moiety and their use in the treatment of tyrosine related diseases and disorders such as cancer. The said derivatives may further act as HDAC inhibitors.

15 Claims, No Drawings

TYROSINE KINASE INHIBITORS CONTAINING A ZINC BINDING MOIETY

RELATED APPLICATIONS

This application is a divisional of U.S. Application No. 11/852,450, filed Sep. 10, 2007, (now U.S. Pat. No. 7,888, 361) which claims the benefit of U.S. Provisional Application No. 60/843,730, filed on Sep. 11, 2006 and U.S. Provisional Application No. 60/895,901, filed on Mar. 20, 2007. The entire teachings of the above applications are incorporated herein by reference.

BACKGROUND OF THE INVENTION

Protein kinases (PK) are enzymes that catalyze the phosphorylation of hydroxyl groups of tyrosine, serine, and threonine residues of proteins. Many aspects of cell life such as cell growth, differentiation, proliferation, cell cycle and survival, depend on protein kinase activities. Furthermore, abnormal protein kinase activity has been related to a host of disorders such as cancer and inflammation. Therefore, there is a great deal of effort directed to identifying ways to modulate protein kinase activities.

Growth factor receptors with PTK activity are known as receptor tyrosine kinases ("RTKs"). They comprise a large family of transmembrane receptors with diverse biological activity. At present, at least nineteen distinct subfamilies of RTKs have been identified. Examples of RTKs subfamily include VEGFR-1, VEGFR-2, Flt-3 c-Kit and PDGFR.

In addition to the RTKs, there also exists a family of entirely intracellular PTKs called "non-receptor tyrosine kinases" or "cellular tyrosine kinases". This latter designation, abbreviated "CTK", will be used herein. CTKs do not contain extracellular and transmembrane domains. At present, over 24 CTKs in 11 subfamilies (Src, Frk, Btk, Csk, Abl, Zap70, Fes/Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene,* 1993, 8:2025-2031.

Chronic myeloid leukaemia (CML) is a stem cell disease characterized by an increased production and accumulation of clonal BCR-ABL-positive cells in haematopoietic tissues. Treatment of CML has been greatly enhanced by the development of Imatinib mesylate, a specific inhibitor of the BCR-ABL tyrosine kinase. However, relapse occurs, mainly as a result of the outgrowth of leukemic subclones with imatinib-resistant BCR-ABL mutations. Dasatinib, an second generation BCR-ABL inhibitor that targets most imatinib-resistant BCR-ABL mutations, induces hematologic and cytogenetic responses in patients with CML or Ph-positive ALL who cannot tolerate or are resistant to imatinib. In addition to inhibiting BCR-ABL, dasatinib has been reported to block activities of the SFKs, Lyn and Src on human prostate cancer cells (Nam, S., et al., *Cancer Res* 2005, 2005, 65 (20), 9185-9188.

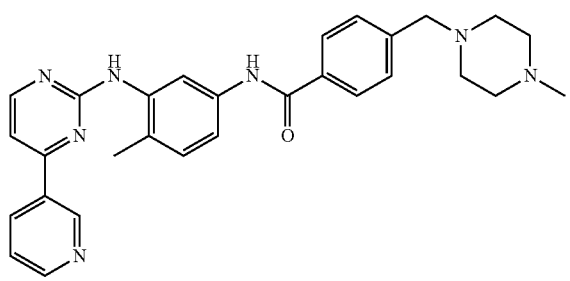

Imatinib (Gleevec®, STI-571)

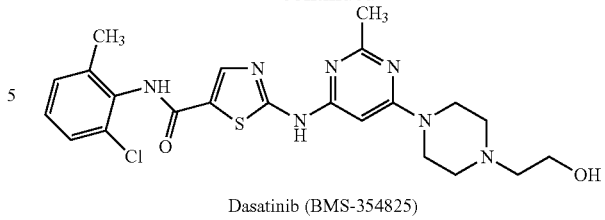

Dasatinib (BMS-354825)

Elucidation of the complex and multifactorial nature of various diseases that involve multiple pathogenic pathways and numerous molecular components suggests that multi-targeted therapies may be advantageous over mono-therapies. Recent combination therapies with two or more agents for many such diseases in the areas of oncology, infectious disease, cardiovascular disease and other complex pathologies demonstrate that this combinatorial approach may provide advantages with respect to overcoming drug resistance, reduced toxicity and, in some circumstances, a synergistic therapeutic effect compared to the individual components.

Certain cancers have been effectively treated with such a combinatorial approach; however, treatment regimes using a cocktail of cytotoxic drugs often are limited by dose limiting toxicities and drug-drug interactions. More recent advances with molecularly targeted drugs have provided new approaches to combination treatment for cancer, allowing multiple targeted agents to be used simultaneously, or combining these new therapies with standard chemotherapeutics or radiation to improve outcome without reaching dose limiting toxicities. However, the ability to use such combinations currently is limited to drugs that show compatible pharmacologic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance owing to the more intricate dosing paradigms required.

In the field of protein and polypeptide-based therapeutics it has become commonplace to prepare conjugates or fusion proteins that contain most or all of the amino acid sequences of two different proteins/polypeptides and that retain the individual binding activities of the separate proteins/polypeptides. This approach is made possible by independent folding of the component protein domains and the large size of the conjugates that permits the components to bind their cellular targets in an essentially independent manner. Such an approach is not, however, generally feasible in the case of small molecule therapeutics, where even minor structural modifications can lead to major changes in target binding and/or the pharmacokinetic/pharmacodynamic properties of the resulting molecule.

Histone acetylation is a reversible modification, with deacetylation being catalyzed by a family of enzymes termed histone deacetylases (HDACs). HDAC's are represented by X genes in humans and are divided into four distinct classes (*J Mol Biol,* 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Csordas, *Biochem. J.,* 1990, 286: 23-38 teaches that histones are subject to post-translational acetylation of the, ε-amino groups of N-terminal lysine residues, a reaction that is catalyzed by histone acetyl transferase (HAT1). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., *Science,* 1996, 272:408-411). In the case of tumor suppressor genes, transcriptional silencing due to histone modification can lead to oncogenic transformation and cancer.

Several classes of HDAC inhibitors currently are being evaluated by clinical investigators. The first FDA approved HDAC inhibitor is Suberoylanilide hydroxamic acid (SAHA, Zolinza®) for the treatment of cutaneous T-cell lymphoma (CTCL). Other HDAC inhibitors include hydroxamic acid derivatives, PXD 101 and LAQ824, are currently in the clinical development. In the benzamide class of HDAC inhibitors, MS-275, MGCD0103 and CI-994 have reached clinical trials. Mourne et al. (Abstract #4725, AACR 2005), demonstrate that thiophenyl modification of benzamides significantly enhance HDAC inhibitory activity against HDAC1.

Recent advances suggest that HDAC inhibitors in combination with other targeted agents may provide advantageous results in the treatment of cancer. For example, co-treatment with SAHA significantly increased EGFR2 antibody trastuzumab-induced apoptosis of BT-474 and SKBR-3 cells and induced synergistic cytotoxic effects against the breast cancer cells (Bali, *Clin. Cancer Res.,* 2005, 11, 3392). HDAC inhibitors, such as SAHA, have demonstrated synergistic antiproliferative and apoptotic effects when used in combination with gefitinib in head and neck cancer cell lines, including lines that are resistant to gefitinib monotherapy (Bruzzese et al., Proc. AACR, 2004). Pretreating gefitinib resistant cell lines with the HDAC inhibitor, MS-275, led to a growth-inhibitory and apoptotic effect of gefitinib similar to that seen in gefitinib-sensitive NSCLC cell lines including those harboring EGFR mutations (Witta S. E., et al., *Cancer Res,* 2006, 66:2, 944-50). The HDAC inhibitor PXD 101 has been shown to act synergistically to inhibit proliferation with the EGFR1 inhibitor Tarceva® (erlotinib) (WO2006082428A2). Synergy between NVP-LAQ824 and imatinib mesylate was demonstrated against BCR/ABL-expressing K562 myeloid leukemia cell lines. (Weisberg et al., *Leukemia.* 2004, 18, 1951).

Current therapeutic regimens of the types described above attempt to address the problem of drug resistance by the administration of multiple agents. However, the combined toxicity of multiple agents due to off-target side effects as well as drug-drug interactions often limit the effectiveness of this approach. Moreover, it often is difficult to combine compounds having differing pharmacokinetics into a single dosage form, and the consequent requirement of taking multiple medications at different time intervals leads to problems with patient compliance that can undermine the efficacy of the drug combinations. In addition, the health care costs of combination therapies may be greater than for single molecule therapies. Moreover, it may be more difficult to obtain regulatory approval of a combination therapy since the burden for demonstrating activity/safety of a combination of two agents may be greater than for a single agent. (Dancey J & Chen H, *Nat. Rev. Drug Dis.,* 2006, 5:649). The development of novel agents that target multiple therapeutic targets selected not by virtue of cross reactivity, but through rational design will help improve patient outcome while avoiding these limitations. Thus, enormous efforts are still directed to the development of selective anti-cancer drugs as well as to new and more efficacious combinations of known anti-cancer drugs.

SUMMARY OF THE INVENTION

The present invention relates to BCR-ABL kinase inhibitors that contain a zinc-binding moiety and their use in the treatment of BCR-ABL related diseases and disorders such as cancer.

The compounds of the present invention may further act as HDAC or matrix metalloproteinase (MMP) inhibitors by virtue of their ability to bind zinc ions. Surprisingly these compounds are active at multiple therapeutic targets and are effective for treating disease. Moreover, in some cases it has even more surprisingly been found that the compounds have enhanced activity when compared to the activities of combinations of separate molecules individually having the BCR-ABL and HDAC activities. In other words, the combination of pharmacophores into a single molecule may provide a synergistic effect as compared to the individual pharmacophores. More specifically, it has been found that it is possible to prepare compounds that simultaneously contain a first portion of the molecule that binds zinc ions and thus permits inhibition of HDAC and/or matrix metalloproteinase (MMP) activity and at least a second portion of the molecule that permits binding to a separate and distinct target that inhibits BCR-ABL and thus provides therapeutic benefit. Preferably, the compounds of the present invention inhibit both BCR-ABL and HDAC activity.

Accordingly, the present invention provides a compound having the general formulae (I) and (II):

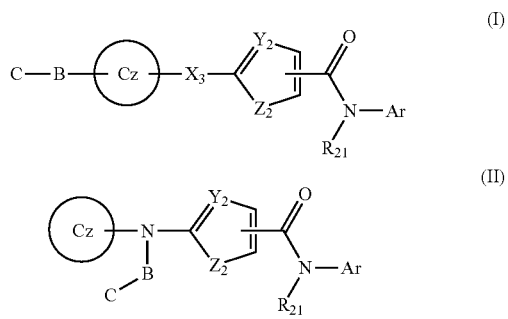

or its geometric isomers, enantiomers, diastereomers, racemates, pharmaceutically acceptable salts, prodrugs and solvates thereof, wherein Cz is selected from aryl, substituted aryl, heteroaryl, substituted heteroaryl, heterocylic and substituted heterocyclic;

Ar is aryl, substituted aryl heteroaryl or substituted heteroaryl;

$X_3$ is NH, alkylamino, O or S;

$Z_2$ is O, S, NH or alkylamino;

$Y_2$ is N or $CR_{20}$; where $R_{20}$ is selected from hydrogen, halogen, aliphatic, substituted aliphatic, aryl, substituted aryl, heteroaryl, substituted heteroaryl;

$R_{21}$ is hydrogen or aliphatic;

B is a direct bond or straight- or branched-, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic;

In one embodiment, the linker B is between 1-24 atoms, preferably 4-24 atoms, preferably 4-18 atoms, more preferably 4-12 atoms, and most preferably about 4-10 atoms.

C is selected from:

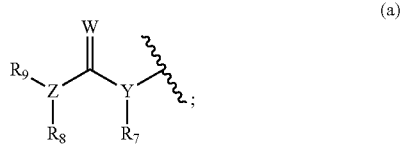

(a)

where W is O or S; Y is absent, N, or CH; Z is N or CH; $R_7$ and $R_9$ are independently hydrogen, OR', aliphatic or substituted aliphatic, wherein R' is hydrogen, aliphatic, substituted aliphatic or acyl; provided that if $R_7$ and $R_9$ are both present, one of $R_7$ or $R_9$ must be OR' and if Y is absent, $R_9$ must be OR'; and $R_{21}$ is hydrogen, acyl, aliphatic, or substituted aliphatic;

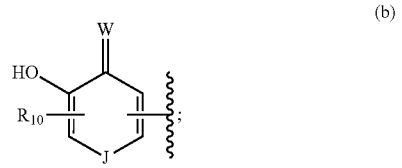

(b)

where W is O or S; J is O, NH or $NCH_3$; and $R_{10}$ is hydrogen or lower alkyl;

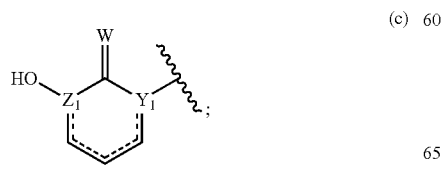

(c)

where W is O or S; $Y_1$ and $Z_1$ are independently N, C or CH; and

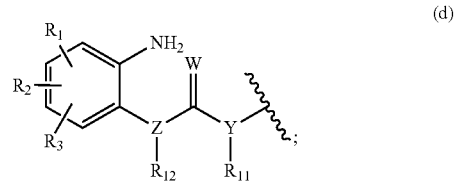

(d)

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $N_3$, $NO_2$, sulfonyl, acyl, aliphatic, substituted aliphatic, aryl, substituted aryl, heteroaryl, substituted heteroaryl, heterocyclic, and substituted heterocyclic.

DETAILED DESCRIPTION OF THE INVENTION

In a first embodiment of the compounds of the present invention are compounds represented by formulae (I) and (II) as illustrated above, or its geometric isomers, enantiomers, diastereomers, racemates, pharmaceutically acceptable salts, prodrugs and solvates thereof.

In a second embodiment of the compounds of the present invention are compounds represented by formula (III) as illustrated below, or its geometric isomers, enantiomers, diastereomers, racemates, pharmaceutically acceptable salts, prodrugs and solvates thereof:

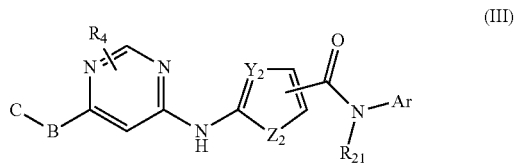

(III)

wherein $R_4$ is hydrogen, aliphatic or substituted aliphatic; C, B, $Y_2$, $Z_2$, Ar and $R_{21}$ are as previously defined.

In a third embodiment of the compounds of the present invention are compounds represented by formula (IV) as illustrated below, or its geometric isomers, enantiomers, diastereomers, racemates, pharmaceutically acceptable salts, prodrugs and solvates thereof:

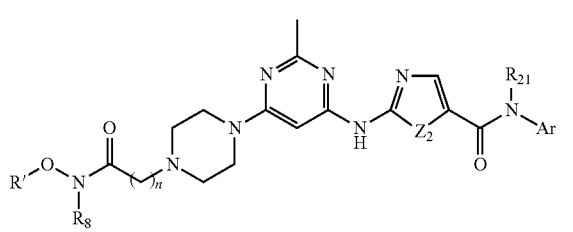

(IV)

wherein n is 1-9; R', $Z_2$, Ar and $R_{21}$ are as previously defined.

In a fourth embodiment of the compounds of the present invention are compounds represented by formula (V) as illustrated below, or its geometric isomers, enantiomers, diastereomers, racemates, pharmaceutically acceptable salts, prodrugs and solvates thereof:

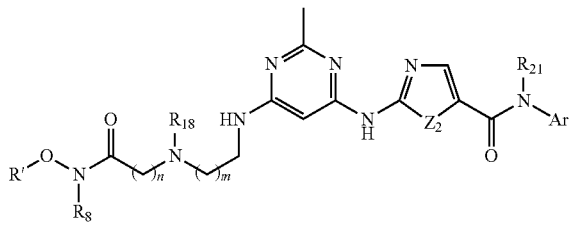

(V)

wherein m and n are independently 1-9; $R_{18}$ is independently $R_8$; R', $Z_2$, Ar $R_8$, and $R_{21}$ are as previously defined.

In a fifth embodiment of the compounds of the present invention are compounds represented by formula (VI) as illustrated below, or its geometric isomers, enantiomers, diastereomers, racemates, pharmaceutically acceptable salts, prodrugs and solvates thereof:

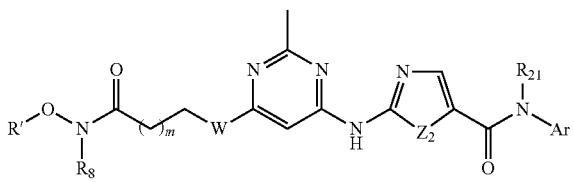

(VI)

wherein m is 0-9; W is O, NH, alkylamino, S, SO, $SO_2$; $Z_2$, Ar R' $R_8$, and $R_{21}$ are as previously defined.

In a sixth embodiment of the compounds of the present invention are compounds represented by formula (VII) as illustrated below, or its geometric isomers, enantiomers, diastereomers, racemates, pharmaceutically acceptable salts, prodrugs and solvates thereof:

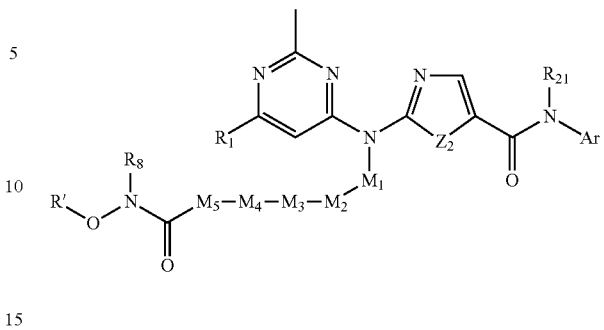

(VII)

wherein $M_1$ is absent, O, NH, alkylamino, or $C_1$-$C_6$ alkyl, $C_2$-$C_6$ alkenyl, $C_2$-$C_6$ alkynyl; $M_2$ is absent, $C_1$-$C_6$ alkyl, O, NH, alkylamine, S, SO, $SO_2$, heterocyclic, heteroaryl, aryl, or C=O; $M_3$ is absent, O, NH, alkyamino, C=O, $C_1$-$C_6$ alkyl, $C_2$-$C_6$ alkenyl, or $C_2$-$C_6$ alkynyl; $M_4$ is absent, O, NH, alkyamino, heterocyclic, heteroaryl or aryl; $M_5$ is absent, $C_1$-$C_8$ alkyl, $C_2$-$C_8$ alkenyl, $C_2$-$C_8$ alkynyl, heterocyclic, heteroaryl or aryl; R', $R_1$, $Z_2$, Ar and $R_{21}$ are as previously defined.

In a seventh embodiment of the compounds of the present invention are compounds represented by formula (VIII) as illustrated below, or its geometric isomers, diastereomers, racemates, pharmaceutically acceptable salts, prodrugs and solvates thereof:

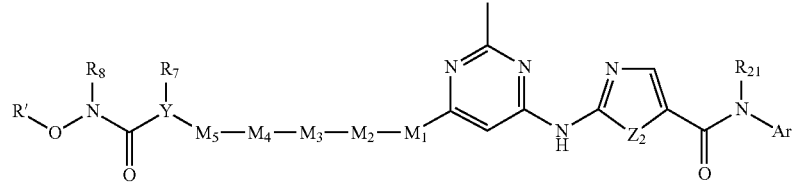

(VIII)

wherein $M_1$ is absent, O, NH, alkylamino, or $C_1$-$C_6$ alkyl, $C_2$-$C_6$ alkenyl, $C_2$-$C_6$ alkynyl; $M_2$ is absent, $C_1$-$C_6$ alkyl, $C_2$-$C_6$ alkenyl, $C_2$-$C_6$ alkynyl, O, NH, alkylamine, S, SO, $SO_2$, heterocyclic, heteroaryl, aryl or C=O; $M_3$ is absent, O, NH, alkyamino, S, SO, $SO_2$, $C_1$-$C_8$ alkyl, $C_2$-$C_8$ alkenyl, $C_2$-$C_8$ alkynyl, heterocyclic, heteroaryl, aryl or C=O; $M_4$ is absent, O, NH, alkyamino, CO, S, SO, $SO_2$, heterocyclic, heteroaryl or aryl; $M_5$ is absent, $C_1$-$C_6$ alkyl, $C_2$-$C_6$ alkenyl, $C_2$-$C_6$ alkynyl, heterocyclic, heteroaryl or aryl; R', $Z_2$, Ar and $R_{21}$ are as previously defined.

In an eighth embodiment of the compounds of the present invention are compounds represented by formula (IX) as illustrated below, or its geometric isomers, enantiomers, diastereomers, racemates, pharmaceutically acceptable salts, prodrugs and solvates thereof:

(IX)

Cz is selected from aryl, substituted aryl, heteroaryl, substituted heteroaryl, heterocylic and substituted heterocyclic;
Ar is aryl, substituted aryl heteroaryl or substituted heteroaryl;
$X_3$ is NH, O or S;
$Z_2$ is O, S, or NH;
$Y_2$ is N or $CR_{20}$; where $R_{20}$ is selected from hydrogen, halogen, aliphatic, substituted aliphatic, aryl, substituted aryl, heteroaryl, substituted heteroaryl;
$R_8$ is hydrogen or aliphatic;
B is a direct bond or straight- or branched-, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, or alkynylheterocyclylalkynyl, which one or more methylenes can be interrupted or terminated by O, S, S(O), $SO_2$, N($R_8$), C(O), substituted or unsubstituted aryl, substituted or unsubstituted heteroaryl, substituted or unsubstituted heterocyclic; where $R_8$ is hydrogen or aliphatic group;
C is selected from:

(a)

where W is O or S; Y is absent, N, or CH; Z is N or CH; $R_7$ and $R_9$ are independently hydrogen, hydroxy, aliphatic group, provided that if $R_7$ and $R_9$ are both present, one of $R_7$ or $R_9$ must be hydroxy and if Y is absent, $R_9$ must be hydroxy; and $R_8$ is hydrogen or aliphatic group;

(b)

where W is O or S; J is O, NH or $NCH_3$; and $R_{10}$ is hydrogen or lower alkyl;

(c)

where W is O or S; $Y_1$ and $Z_1$ are independently N, C or CH; and (d)

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic.

In a ninth embodiment of the compounds of the present invention are compounds represented by formula (X) as illustrated below, or its geometric isomers, enantiomers, diastereomers, racemates, pharmaceutically acceptable salts, prodrugs and solvates thereof:

(X)

wherein $R_4$ is hydrogen, aliphatic or substituted aliphatic; C, B, $Y_2$, $Z_2$, Ar and $R_8$ are as previously defined.

In a tenth embodiment of the compounds of the present invention are compounds represented by formula (XI) as illustrated below, or its geometric isomers, enantiomers, diastereomers, racemates, pharmaceutically acceptable salts, prodrugs and solvates thereof:

(XI)

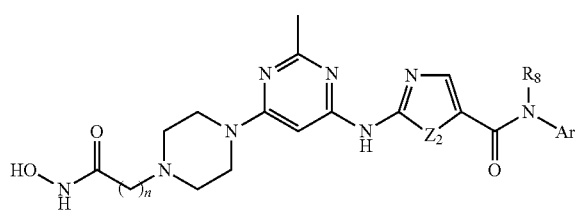

wherein n is 1-9; $Z_2$, Ar and $R_8$ are as previously defined.

In an eleventh embodiment of the compounds of the present invention are compounds represented by formula (XII) as illustrated below, or its geometric isomers, enantiomers, diastereomers, racemates, pharmaceutically acceptable salts, prodrugs and solvates thereof:

(XII)

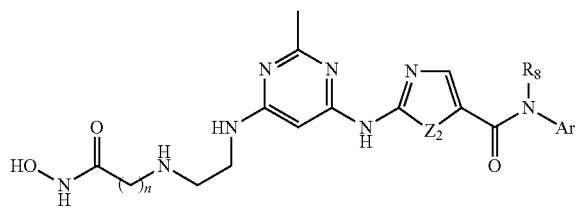

wherein n is 1-9; $Z_2$, Ar and $R_8$ are as previously defined.

In a twelfth embodiment of the compounds of the present invention are compounds represented by formula (XIII) as illustrated below, or its geometric isomers, enantiomers, diastereomers, racemates, pharmaceutically acceptable salts, prodrugs and solvates thereof:

(XIII)

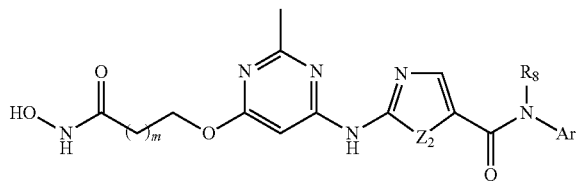

wherein m is 0-9; $Z_2$, Ar and $R_8$ are as previously defined.

In a thirteenth embodiment of the compounds of the present invention are compounds represented by formula (XIV) as illustrated below, or its geometric isomers, enantiomers, diastereomers, racemates, pharmaceutically acceptable salts, prodrugs and solvates thereof:

(XIV)

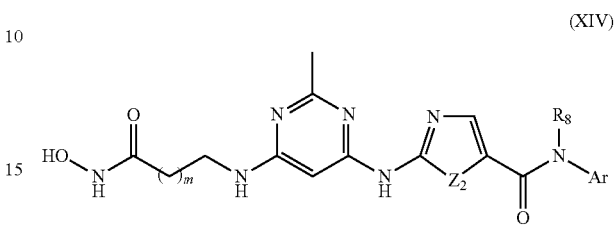

wherein m is 0-9; $Z_2$, Ar and $R_8$ are as previously defined.

In a fourteenth embodiment of the compounds of the present invention are compounds represented by formula (XV) as illustrated below, or its geometric isomers, enantiomers, diastereomers, racemates, pharmaceutically acceptable salts, prodrugs and solvates thereof:

(XV)

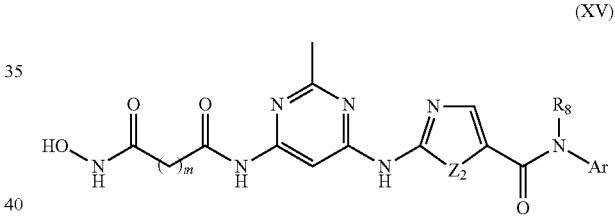

wherein m is 0-9; $Z_2$, Ar and $R_8$ are as previously defined.

Representative compounds according to the invention are those selected from the Table A below or its geometric isomers, enantiomers, diastereomers, racemates, pharmaceutically acceptable salts, prodrugs and solvates thereof:

TABLE A

| Compound # | Structure |
|---|---|
| 1 | 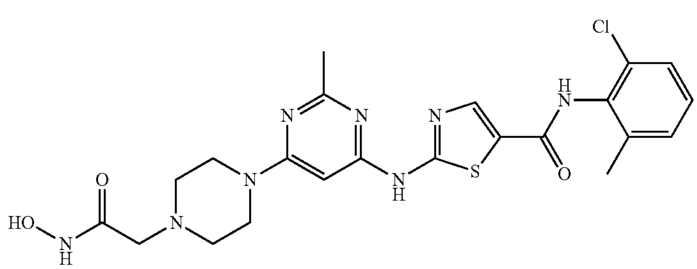 [SMILES: Cc1nc(Nc2ncc(C(=O)Nc3c(C)cccc3Cl)s2)cc(N2CCN(CC(=O)NO)CC2)n1] |

TABLE A-continued

| Compound # | Structure |
|---|---|
| 2 | (chemical structure) |
| 3 | (chemical structure) |
| 4 | (chemical structure) |
| 5 | (chemical structure) |
| 6 | (chemical structure) |
| 7 | (chemical structure) |

TABLE A-continued

| Compound # | Structure |
|---|---|
| 8 | 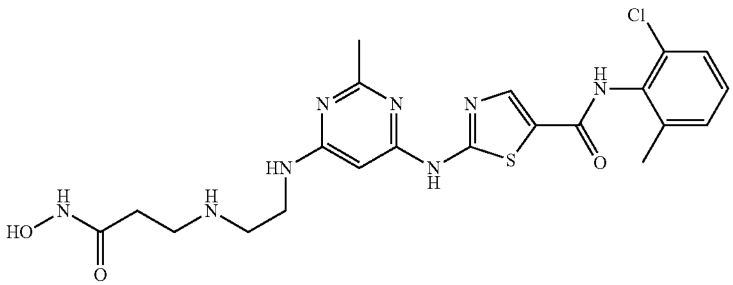 [SMILES: Cc1nc(NCCNCCC(=O)NO)cc(Nc2ncc(C(=O)Nc3c(C)cccc3Cl)s2)n1] |
| 9 | 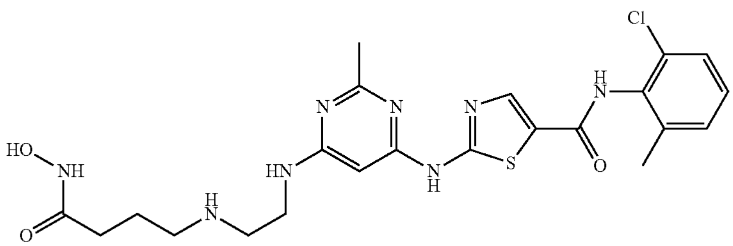 |
| 10 | 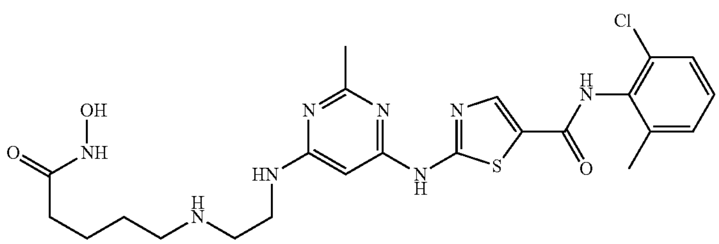 [SMILES: Cc1nc(NCCNCCCCC(=O)NO)cc(Nc2ncc(C(=O)Nc3c(C)cccc3Cl)s2)n1] |
| 11 | 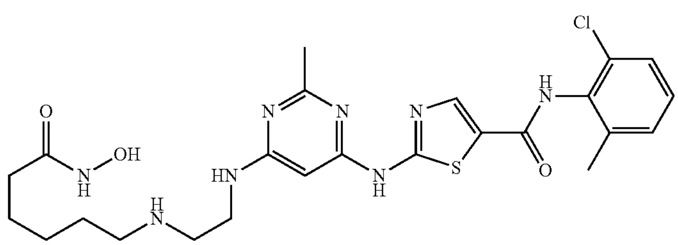 [SMILES: Cc1nc(NCCNCCCCCC(=O)NO)cc(Nc2ncc(C(=O)Nc3c(C)cccc3Cl)s2)n1] |
| 12 | 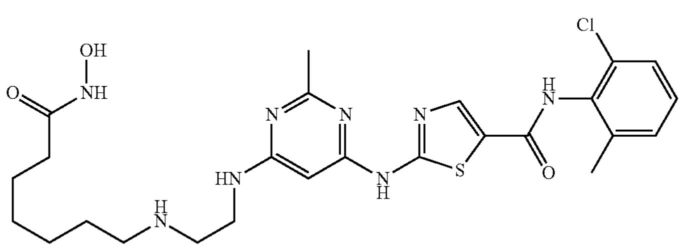 |
| 13 | 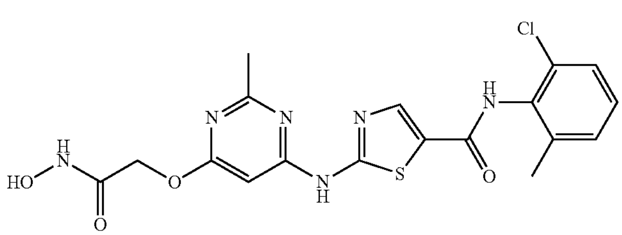 [SMILES: Cc1nc(Nc2ncc(C(=O)Nc3c(C)cccc3Cl)s2)cc(OCC(=O)NO)n1] |

TABLE A-continued

| Compound # | Structure |
|---|---|
| 14 | 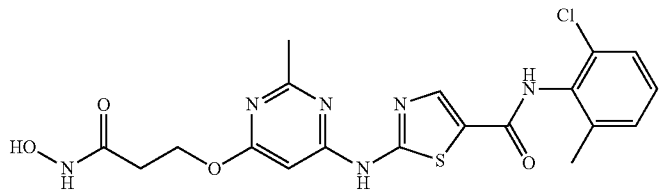 [SMILES: Cc1nc(Nc2ncc(C(=O)Nc3c(C)cccc3Cl)s2)cc(OCCC(=O)NO)n1] |
| 15 | 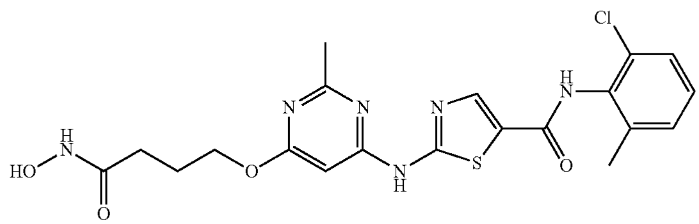 [SMILES: Cc1nc(Nc2ncc(C(=O)Nc3c(C)cccc3Cl)s2)cc(OCCCC(=O)NO)n1] |
| 16 | 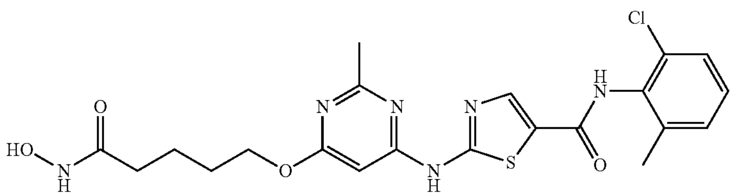 [SMILES: Cc1nc(Nc2ncc(C(=O)Nc3c(C)cccc3Cl)s2)cc(OCCCCC(=O)NO)n1] |
| 17 | 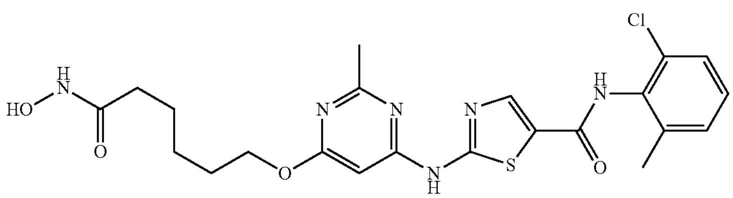 [SMILES: Cc1nc(Nc2ncc(C(=O)Nc3c(C)cccc3Cl)s2)cc(OCCCCCC(=O)NO)n1] |
| 18 | 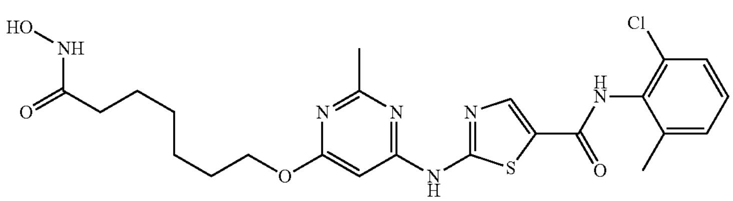 [SMILES: Cc1nc(Nc2ncc(C(=O)Nc3c(C)cccc3Cl)s2)cc(OCCCCCCC(=O)NO)n1] |
| 19 | 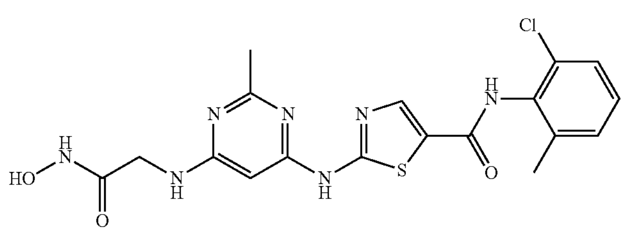 [SMILES: Cc1nc(NCC(=O)NO)cc(Nc2ncc(C(=O)Nc3c(C)cccc3Cl)s2)n1] |
| 20 | 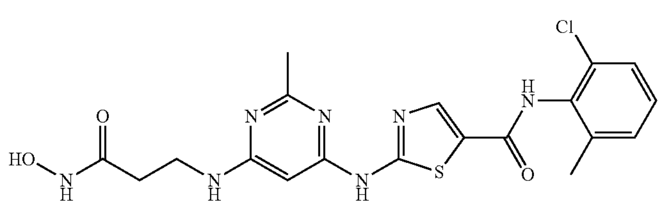 [SMILES: Cc1nc(NCCC(=O)NO)cc(Nc2ncc(C(=O)Nc3c(C)cccc3Cl)s2)n1] |

TABLE A-continued

| Compound # | Structure |
|---|---|
| 21 | 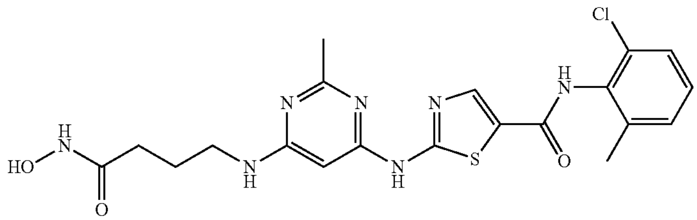 [SMILES: Cc1nc(NCCCC(=O)NO)cc(Nc2ncc(C(=O)Nc3c(C)cccc3Cl)s2)n1] |
| 22 | 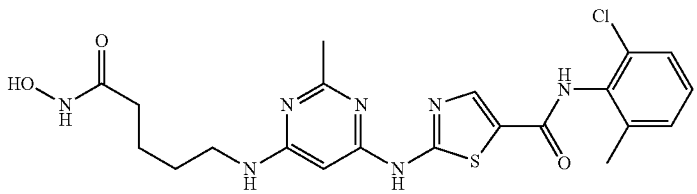 [SMILES: Cc1nc(NCCCCC(=O)NO)cc(Nc2ncc(C(=O)Nc3c(C)cccc3Cl)s2)n1] |
| 23 | 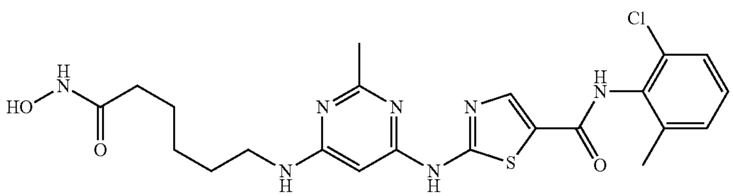 |
| 24 | 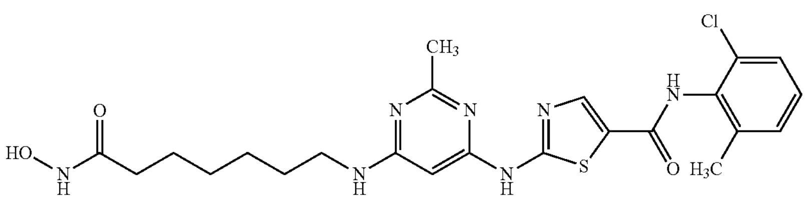 [SMILES: Cc1nc(NCCCCCCC(=O)NO)cc(Nc2ncc(C(=O)Nc3c(C)cccc3Cl)s2)n1] |
| 25 | 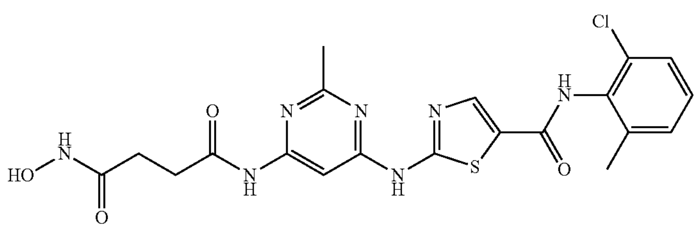 [SMILES: Cc1nc(NC(=O)CCC(=O)NO)cc(Nc2ncc(C(=O)Nc3c(C)cccc3Cl)s2)n1] |
| 26 | 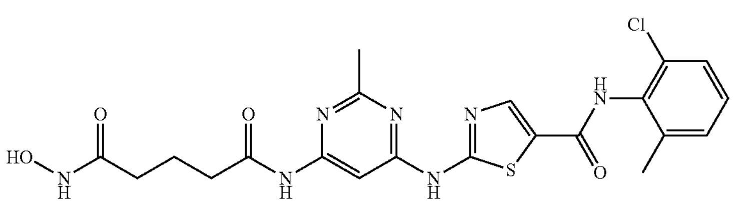 [SMILES: Cc1nc(NC(=O)CCCC(=O)NO)cc(Nc2ncc(C(=O)Nc3c(C)cccc3Cl)s2)n1] |
| 27 | 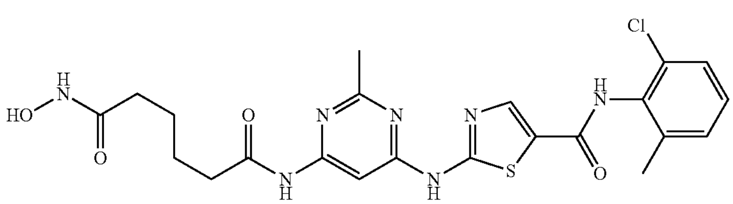 [SMILES: Cc1nc(NC(=O)CCCCC(=O)NO)cc(Nc2ncc(C(=O)Nc3c(C)cccc3Cl)s2)n1] |

TABLE A-continued
| Compound # | Structure |
|---|---|
| 28 | 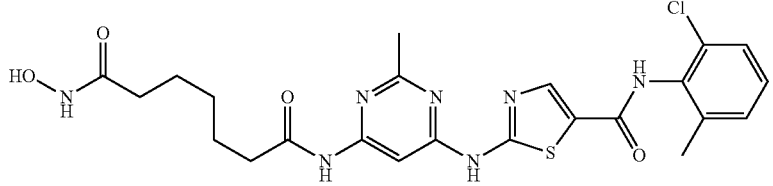 [SMILES: Cc1nc(NC(=O)CCCCCC(=O)NO)cc(Nc2ncc(C(=O)Nc3c(C)cccc3Cl)s2)n1] |
| 29 | 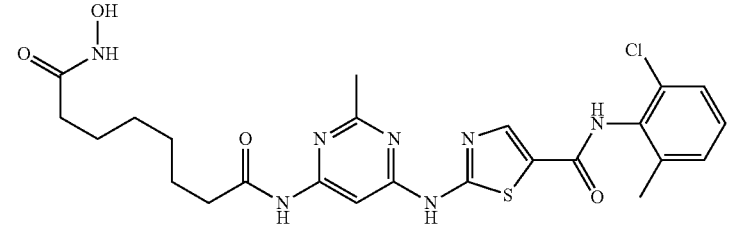 [SMILES: Cc1nc(NC(=O)CCCCCCC(=O)NO)cc(Nc2ncc(C(=O)Nc3c(C)cccc3Cl)s2)n1] |
| 30 | 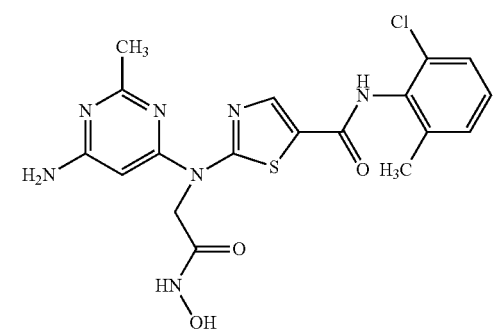 |
| 31 | 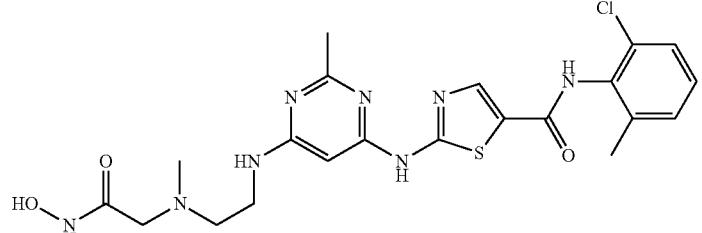 |
| 32 | 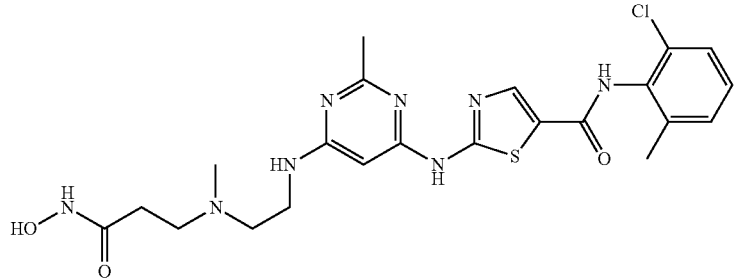 |
| 33 | 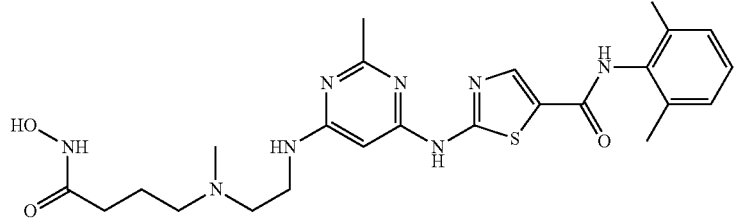 |

TABLE A-continued

| Compound # | Structure |
|---|---|
| 34 | 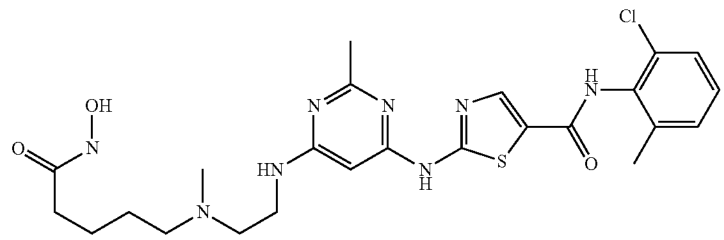 [SMILES: Cc1nc(NCCN(C)CCCCC(=O)NO)cc(Nc2ncc(C(=O)Nc3c(C)cccc3Cl)s2)n1] |
| 35 | 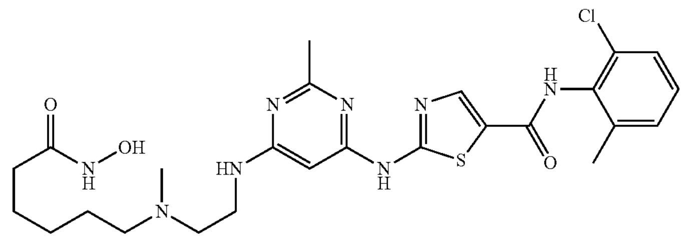 [SMILES: Cc1nc(NCCN(C)CCCCCC(=O)NO)cc(Nc2ncc(C(=O)Nc3c(C)cccc3Cl)s2)n1] |
| 36 | 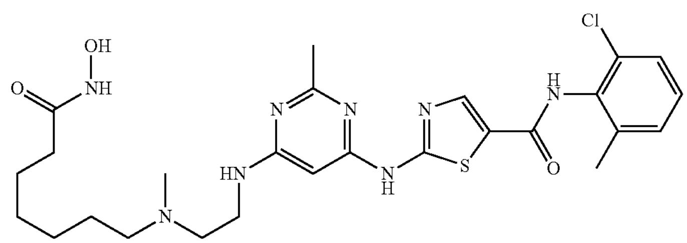 [SMILES: Cc1nc(NCCN(C)CCCCCCC(=O)NO)cc(Nc2ncc(C(=O)Nc3c(C)cccc3Cl)s2)n1] |
| 37 | 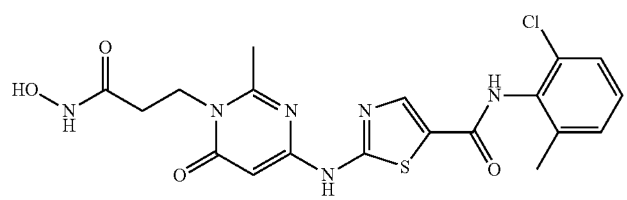 [SMILES: Cc1cccc(Cl)c1NC(=O)c1cnc(Nc2cc(=O)n(CCC(=O)NO)c(C)n2)s1] |
| 38 | 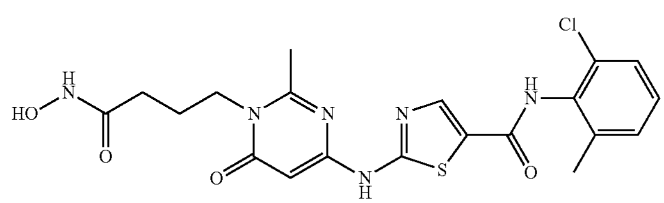 [SMILES: Cc1cccc(Cl)c1NC(=O)c1cnc(Nc2cc(=O)n(CCCC(=O)NO)c(C)n2)s1] |
| 39 | 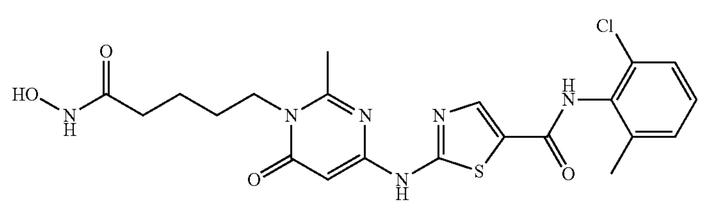 [SMILES: Cc1cccc(Cl)c1NC(=O)c1cnc(Nc2cc(=O)n(CCCCC(=O)NO)c(C)n2)s1] |
| 40 | 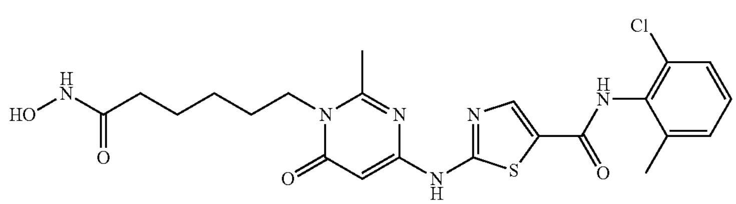 [SMILES: Cc1cccc(Cl)c1NC(=O)c1cnc(Nc2cc(=O)n(CCCCCC(=O)NO)c(C)n2)s1] |

| Compound # | Structure |
|---|---|
| 41 | 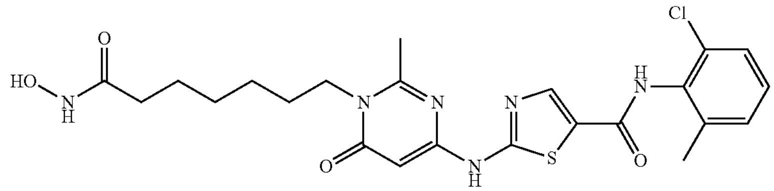 [SMILES: Cc1cccc(Cl)c1NC(=O)c1cnc(Nc2cc(=O)n(CCCCCCC(=O)NO)c(C)n2)s1] |
| 42 | 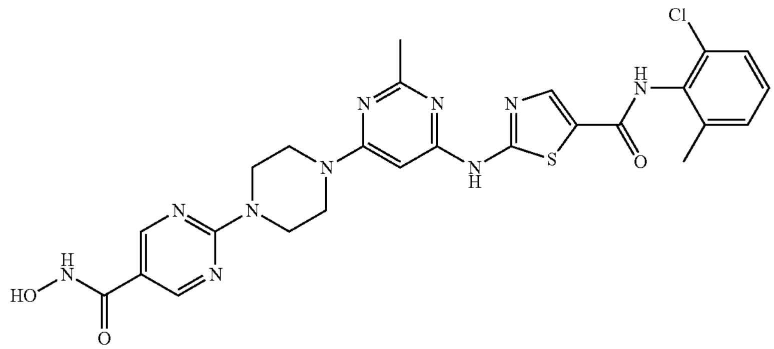 [SMILES: Cc1nc(Nc2ncc(C(=O)Nc3c(C)cccc3Cl)s2)cc(N2CCN(c3ncc(C(=O)NO)cn3)CC2)n1] |
| 43 | 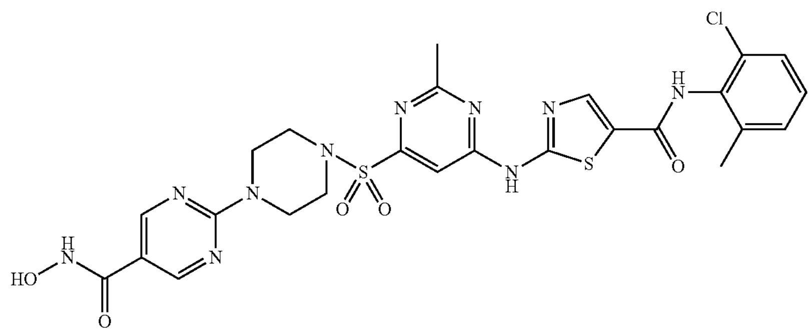 [SMILES: Cc1nc(Nc2ncc(C(=O)Nc3c(C)cccc3Cl)s2)cc(S(=O)(=O)N2CCN(c3ncc(C(=O)NO)cn3)CC2)n1] |

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkins lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In another aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1,GFF-R2/BEK/CEK3, FGF-R3/CEK2, FGF-R-4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan; anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more other therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

In another aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

Matrix metalloproteinases (MMPs) are a family of zinc-dependent neutral endopeptidases collectively capable of degrading essentially all matrix components. Over 20 MMP modulating agents are in pharmaceutical develop, almost half of which are indicated for cancer. The University of Toronto researchers have reported that HDACs regulate MMP expression and activity in 3T3 cells. In particular, inhibition of HDAC by trichostatin A (TSA), which has been shown to prevent tumorigenesis and metastasis, decreases mRNA as well as zymographic activity of gelatinase A (MMP2; Type IV collagenase), a matrix metalloproteinase, which is itself, implicated in tumorigenesis and metastasis (Ailenberg M., Silverman M., *Biochem Biophys Res Commun.* 2002 , 298: 110-115). Another recent article that discusses the relationship of HDAC and MMPs can be found in Young D. A., et al., *Arthritis Research & Therapy,* 2005, 7: 503. Furthermore, the commonality between HDAC and MMPs inhibitors is their zinc-binding functionality. Therefore, in another aspect of the invention, compounds of the invention can be used as MMP inhibitors.

In one aspect, the compounds may also be used in the treatment of a disorder involving, relating to or, associated with dysregulation of histone deacetylase (HDAC).

There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Anti-proliferative disorders (e.g. cancers); Neuro-degenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, psoriasis, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including heart failure, restenosis and arteriosclerosis; Fibrotic diseases including liver fibrosis, cystic fibrosis and angiofibroma; Infectious diseases including Fungal infections, such as Candida Albicans, Bacterial infections, Viral infections, such as Herpes Simplex, Protozoal infections, such as Malaria, Leishmania infection, Trypanosoma brucei infection, Toxoplasmosis and coccidiosis and Haematopoietic disorders including thalassemia, anemia and sickle cell anemia.

In one embodiment compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In another aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, staphylococcus aureus infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In another aspect, the invention provides the use of compounds of the invention in the treatment of a variety of neurodegenerative diseases, a non-exhaustive list of which is: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motoneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peritoneal muscular atrophy (Charcot-Marie-Tooth), hypertrophic interstitial polyneuropathy (Dejerine-Sottas), and miscellaneous forms of chronic progressive neuropathy; VIII Syndromes of progressive visual loss such as pigmentary degeneration of the retina (retinitis pigmentosa), and hereditary optic atrophy (Leber's disease). Furthermore, compounds of the invention can be implicated in chromatin remodeling.

In one aspect, the compounds may also be used in the treatment of a disorder involving, relating to or associated with Src.

Members of the Src-family of tyrosine kinases, in particular, have been shown to be important in cell signal transduction as it relates to inflammatory response and inflammation-related conditions. Gene disruption studies suggest that inhibition of some members of the src family of kinases would potentially lead to a therapeutic benefit. Src(−/−) mice have abnormalities in bone remodeling or osteopetrosis (Soriano, P. *Cell,* 1991, 64, 693), suggesting that inhibition of this kinase might be useful in diseases of bone resorption, such as osteoporosis. Lck(−/−) mice have defects in T cell maturation and activation (Anderson, S J et al. *Adv. Immunol.,* 1994, 56, 151), suggesting that inhibition of this kinase might be useful in diseases of T cell mediated inflammation. In addition, human patients have been identified with mutations affecting Lck kinase activity (Goldman, F D et al. *J. Clin. Invest.* 1998, 102, 421). These patients suffer from a severe combined immunodeficiency disorder (SCID).

Src-family kinases are also important for signaling downstream of other immune cell receptors. Fyn, like Lck, is involved in TCR signaling in T cells (Appleby, M W et al. *Cell,* 1992, 70, 751). Hck and Fgr are involved in Fc.gamma. receptor signaling leading to neutrophil activation (Vicentini, L. et al. *J. Immunol.* 2002, 168, 6446). Lyn and Src also participate in Fc.gamma. receptor signaling leading to release of histamine and other allergic mediators (Turner, H. and Kinet, J-P *Nature* 1999, 402, B24). These findings suggest that Src family kinase inhibitors may be useful in treating allergic diseases and asthma.

Src kinases are also activated in tumors including sarcoma, melanoma, breast, and colon cancers suggesting that Src kinase inhibitors may be useful anti-cancer agents (Abram, C L and Courtneidge, S A Exp. *Cell Res.,* 2000, 254, 1). Src kinase inhibitors have also been reported to be effective in an animal model of cerebral ischemia (R. Paul et al. *Nature Medicine,* 2001, 7, 222), suggesting that Src kinase inhibitors may be effective at limiting brain damage following stroke.

Src-family kinases other than Lck, such as Hck and Fgr, are important in the Fc.gamma. receptor induced respiratory burst of neutrophils as well as the Fc.gamma. receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease.

In addition, certain Src family kinases, such as Lyn and Fyn(B), may be important in the FCγ receptor induced degranulation of mast cells and basophils that plays an important role in asthma, allergic rhinitis, and other allergic disease. FCγ receptors are stimulated by IgE-antigen complexes. The compounds of the present invention may inhibit the FCγ induced degranulation responses. The ability to inhibit FCγ receptor dependent mast cell and basophil responses may result in additional anti-inflammatory activity for the present compounds beyond their effect on T cells.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, i.e., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

Definitions

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group preferably contains between about 1 and about 24 atoms, more preferably between about 4 to about 24 atoms, more preferably between about 4-12 atoms, more typically between about 4 and about 8 atoms.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The terms "alkoxy" embrace linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "carbonyl", whether used alone or with other terms, such as "alkoxycarbonyl", denotes (C=O).

The term "carbanoyl", whether used alone or with other terms, such as "arylcarbanoylyalkyl", denotes C(O)NH.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms and heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between 1-24 atoms, preferably 4-24 atoms, preferably 4-18 atoms, more preferably 4-12 atoms, and most preferably about 4-10 atoms.

The term "substituted" refers to the replacement of one or more hydrogen radicals in a given structure with the radical of a specified substituent including, but not limited to, halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituents listed above may be further substituted.

The term "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta 3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase a "radiotherapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (TAAs).

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences*, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-(B) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of the invention may be prepared by any process known to be applicable to the preparation of chemically-related compounds. Suitable processes for making certain intermediates include, for example, those illustrated references such as, *J. Med. Chem.* 2004, 47, 6658-6661 and *J. Org. Chem.* 1952, 1320. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic scheme that illustrate the methods by which the compounds of the invention may be prepared, which are intended as an illustration only and not limiting of the scope of the invention.

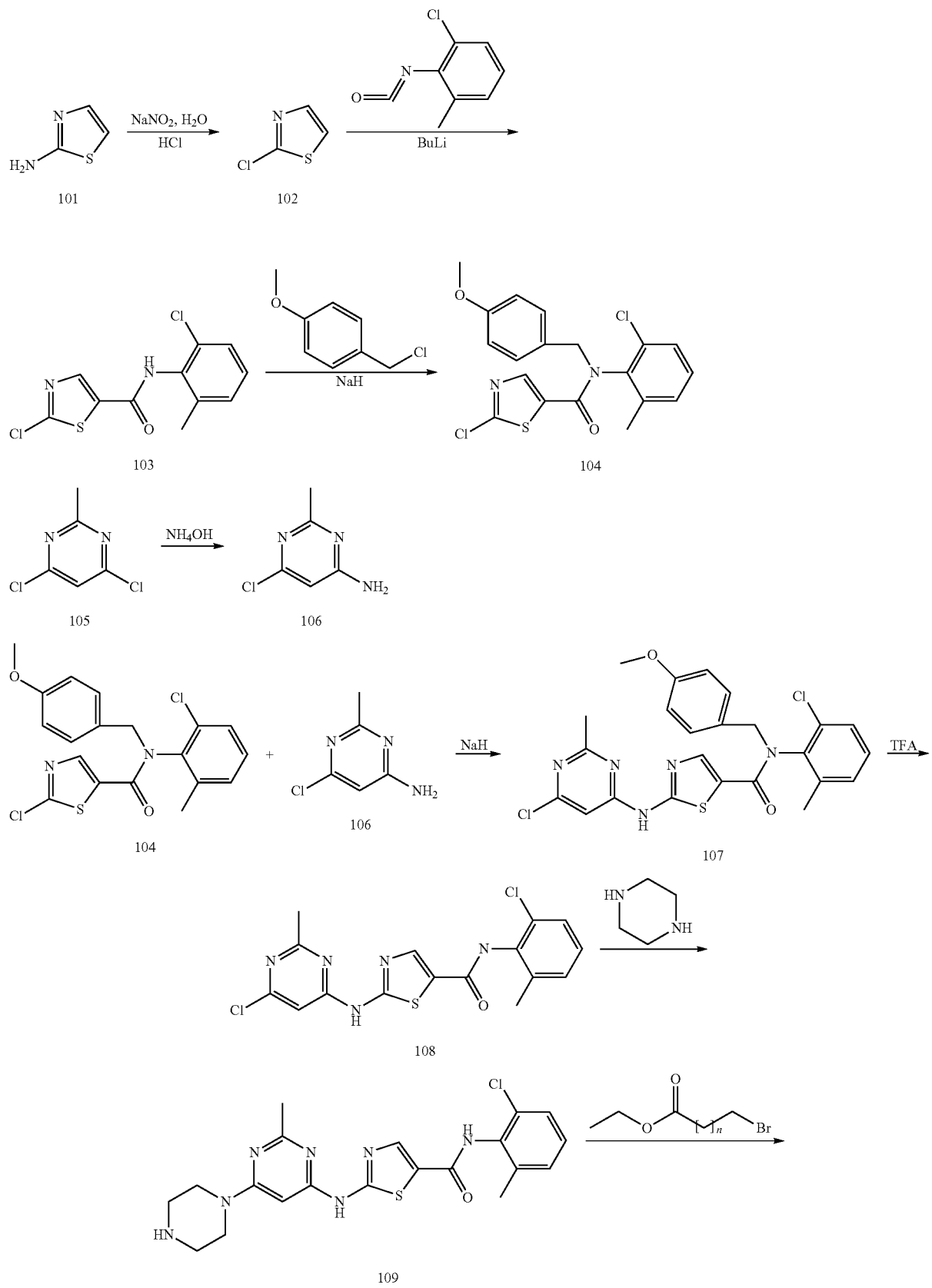
Scheme 1

-continued
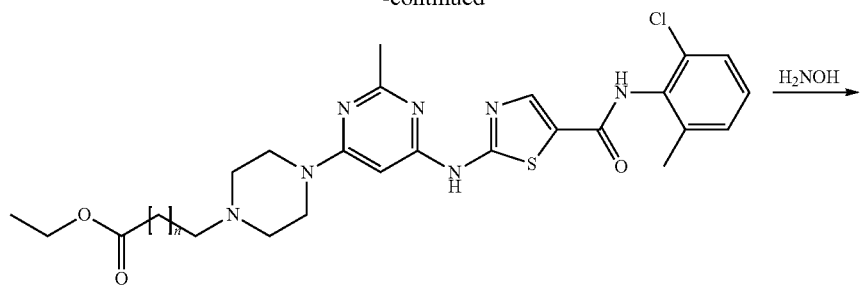
110
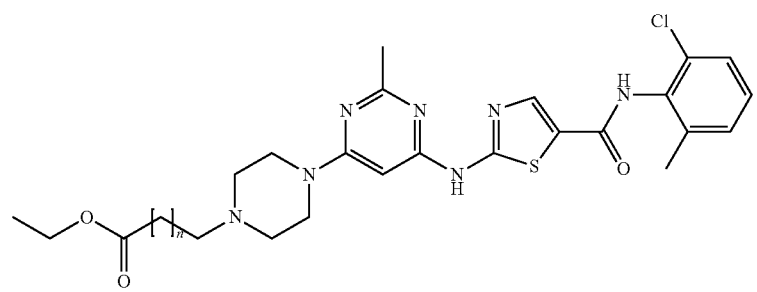
Scheme 2
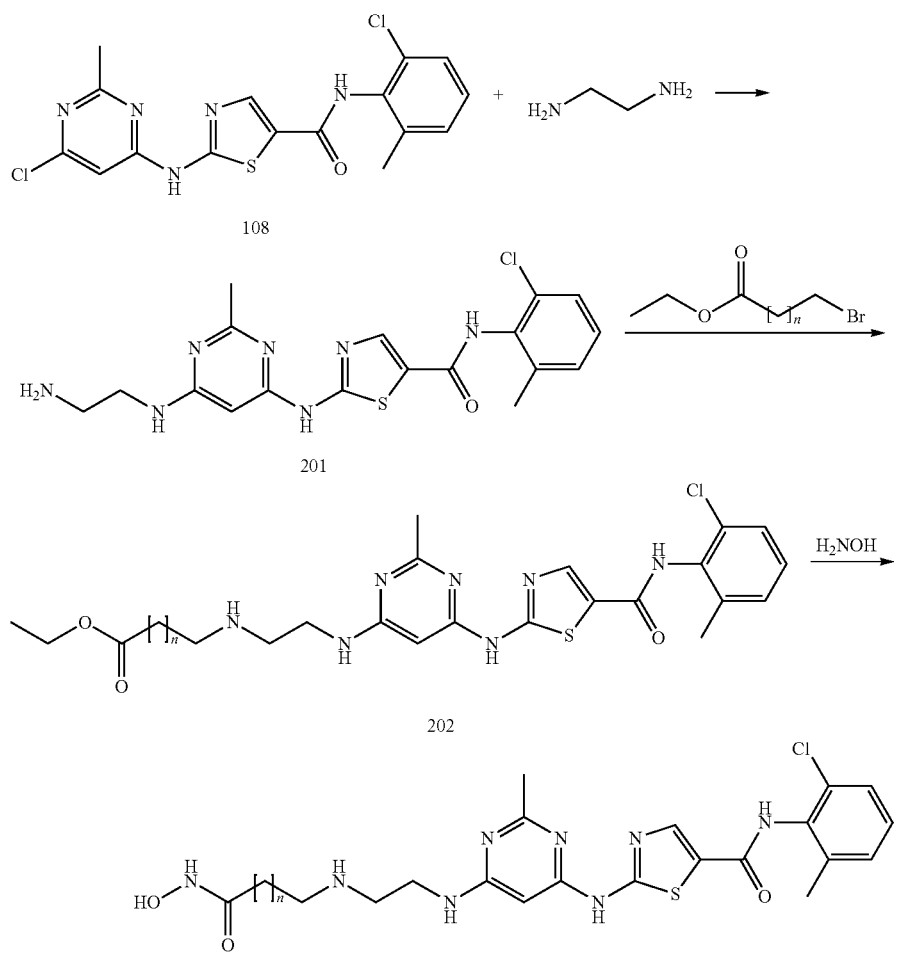
108
201
202

Scheme 3
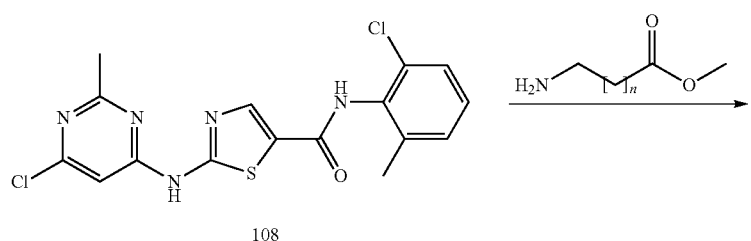
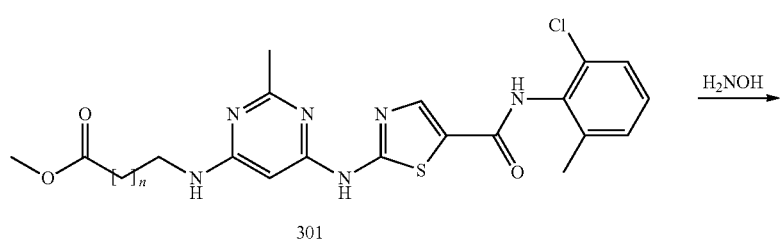
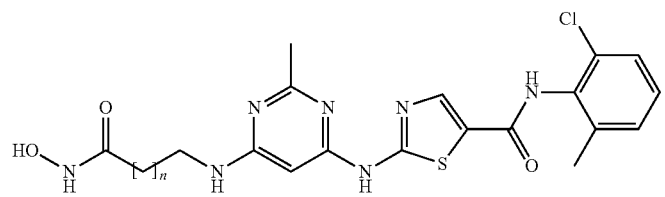
Scheme 4
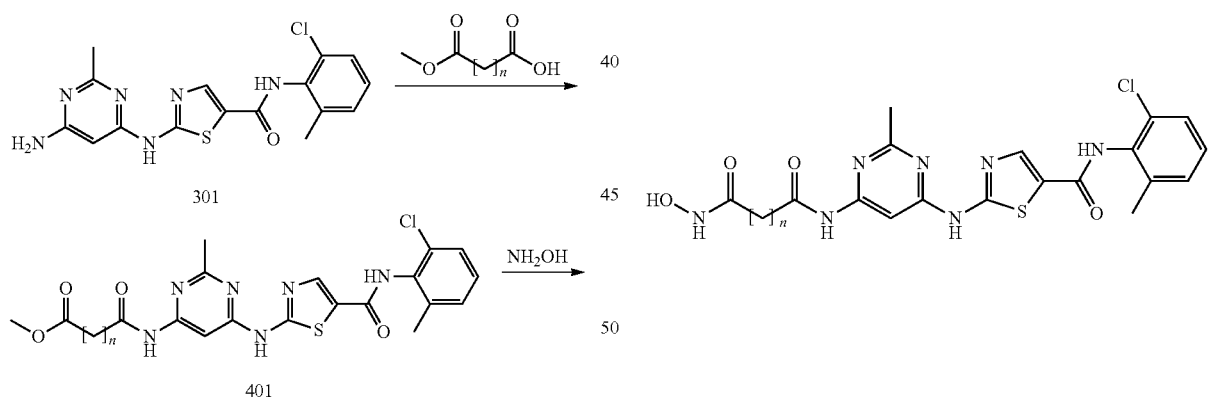
Scheme 5
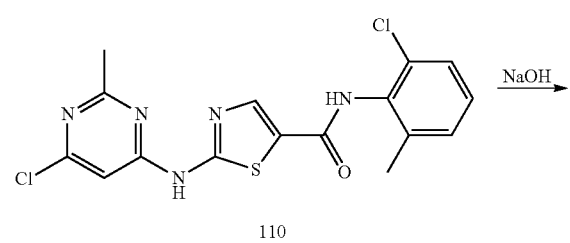

-continued

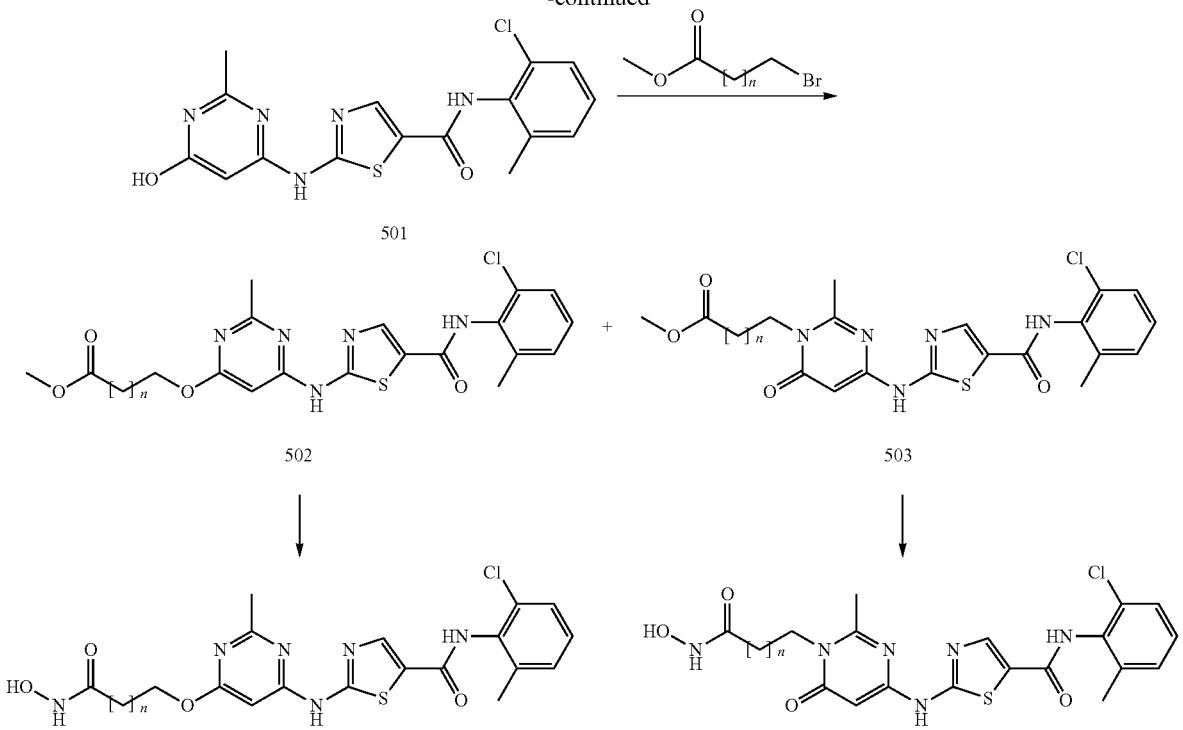

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of N-(2-chloro-6-methylphenyl)-2-(6-(4-(2-(hydroxyamino)-2-oxoethyl)piperazin-1-yl)-2-methylpyrimidin-4-ylamino)thiazole-5-carboxamide (Compound 1)

Step 1a. 2-Chlorothiazole (Compound 102)

A solution of 2-aminothiazole (101) (20.0 g, 200.0 mmol) in saturated aqueous NaCl (20 mL) and HCl (60 mL) was maintained in a room-temperature bath. It was then treated with $NaNO_2$ (250 mmol) in $H_2O$ (50 mL) and concentrated HCl (20 mL) dropwise simultaneously. The reaction was stirred at room temperature for 1 hour, extracted with ether and concentrated at 1 atm. The product was obtained by distilled under vacuum to give 102 as a pale yellow liquid (10.7 g, 45%): $^1$H NMR (CDCl$_3$) δ 7.24 (d, J=3.6 Hz, 1H), 7.57 (d, J=3.3 Hz,1H).

Step 1b. 2-Chloro-N-(2-chloro-6-methylphenyl)thiazole-5-carboxamide (Compound 103)

A solution of 2-chlorothiazole (102) (480 mg, 4.0 mmol) in THF (10 mL) was cooled to −78° C. and treated dropwise with 2.5 M n-butyllithium in hexanes (1.68 mL, 4.2 mmol) over a period of 20 minutes while keeping the temperature below −75° C. After the addition was complete, the mixture was stirred at −78° C. for 15 minutes and then treated with a solution of 2-chloro-6-methylphenylisocyanate (4.4 mmol) in THF (5 mL). The mixture was stirred at −78° C. for 2 hours, quenched with saturated aqueous $NH_4Cl$, warmed to room temperature and partitioned between EtOAc and $H_2O$. The EtOAc phase was separated, washed with brine, dried ($Na_2SO_4$) and concentrated under vacuum to afford a yellow solid. The crude product was purified by column chromatography to give compound 103 as a pale yellow solid (0.95 g, 83%). LCMS: 286 [M+1]$^+$. $^1$H NMR (DMSO-d$_6$): δ 2.22 (s, 3H), 7.29 (m, 2H), 7.41 (dd, J=6.3, J=3.0 Hz, 1H), 8.45 (s, 1H), 10.40 (s, 1H).

Step 1c. 2-Chloro-N-(2-chloro-6-methylphenyl)-N-(4-methoxybenzyl)thiazole-5-carboxamide (Compound 104)

A solution of 2-chloro-N-(2-chloro-6-methylphenyl)thiazole (103) (0.57 g, 2.0 mmol) in DMF (5 mL) was treated with 60% NaH (2.4 mmol) and stirred at room temperature for 30 minutes. The mixture was treated with 4-methoxybenzyl chloride (0.38 g, 2.4 mmol) and tetrabutylammonium iodide (0.15 mg, 0.40 mmol), and then stirred at room temperature for 16 h. The mixture was partitioned between $H_2O$ and EtOAc and then the EtOAc phase was separated, washed with brine, dried ($Na_2SO_4$) and concentrated under vacuum. The crude product was purified by column chromatography to give compound 104 as a yellow solid (0.50 g, 62%). LCMS: 429 [M+Na]$^+$. $^1$H NMR (DMSO-d$_6$): δ 1.73 (s, 3H), 3.60 (s, 3H), 4.48 (d, J=13.8 Hz, 1H), 5.09 (d, J=14.1 Hz,1H), 6.79 (d, J=8.4 Hz, 2H), 7.11 (d, J=8.7 Hz, 2H), 7.29 (d, J=6.6 Hz, 1H), 7.44 (m, 3H).

Step 1d. 6-Chloro-2-methylpyrimidin-4-amine (Compound 106)

A solution of 4,6-dichloro-2-methylpyrimidin (105) (20.0 g, 120 mmol) was placed in a tube with ammonium hydroxide (50 mL). The tube was sealed and heated at 125-128° C. for 10 hours. After cooling, the tube was opened and the reaction mixture (coarse, white crystals) was filtrated, giving the product compound 106 as a white solid (12.4 g, 70%). LCMS: 144 [M+1]$^+$ $^1$H NMR (DMSO-d$_6$): δ 2.27 (s, 3H), 6.24 (s, 1H), 7.08 (s, 2H).

Step 1e. 2-((6-Chloro-2-methylpyrimidin-4-yl)methyl)-N-(2-chloro-6-methylphenyl)-N-(4-methoxybenzyl)thiazole-5-carboxamide (Compound 107)

4-Amino- 6-chloro-2-methylpyrimidine (106) (14.0 mg, 0.10 mmol) was added in portions to a suspension of NaH (60% dispersion, 0.30 mmol) in THF (30 mL) at 0° C. for 30 minutes and then treated with compound 104 (41.0 mg, 0.10 mmol) in portions. The resulting mixture was at reflux for 4 hours, cooled to room temperature and diluted with H$_2$O (10 mL). The mixture was acidified with 1 N HCl (5 mL) and extracted with EtOAc (3×10 mL). The organic layer was dried (Na$_2$SO$_4$) and evaporated. The crude product was purified by column chromatography to give compound 107 as a pale yellow solid (41 mg, 80%): $^1$H NMR (DMSO-d$_6$): δ 1.72 (s,3H), 2.45 (s,3H), 3.71 (s, 3H), 4.40 (d, J=14.1 Hz, 1H) 5.19 (d, J=13.8 Hz,1H), 6.81 (m,3H), 7.14 (d, J=8.4 Hz, 2H), 7.29 (d, J=7.5 Hz, 1H), 7.43 (t, J=7.8, Hz, 1H), 7.47 (s,1H), 7.53 (d, J=6.9 Hz, 1H), 12.07 (ds,1H).

Step 1f. 2-(6-Chloro-2-methylpyrimidin-4-ylamino)-N-(2-chloro-6-methylphenyl)thiazole-5-carboxamide (Compound 108)

A solution of compound 107 (10.0 g, 19.5 mmol) dissolved in 50% TFA in CH$_2$Cl$_2$ (50 mL) was treated with triflic acid (10.0 g, 67.5 mmol). The reaction mixture was stirred at room temperature for 24 hours. The mixture was poured into crushed ice (150 g). The resulting solid was collected by filtration to obtain compound 108 as a yellow solid (5.6 g, 87%). $^1$H NMR (DMSO-d$_6$): δ 2.21 (s,3H), 2.39 (s, 3H), 6.07 (m, 1H), 7.26 (m,2H), 7.37 (d, J=6.6 Hz ,1H), 8.20 (s, 1H), 9.85 (s, 1H), 11.47 (s, 1H).

Step 1g. N-(2-Chloro-6-methylphenyl)-2-(2-methyl-6-(piperazin-1-yl)pyrimidin-4-ylamino)thiazole-5-carboxamide (Compound 109)

A mixture of compound 108 (2.60 g, 6.6 mmol), piperazine (5.60 g, 66.0 mmol), potassium carbonate (1.82 g, 13.2 mmol) and DMF (15 mL) was stirred at 135° C. for 12 hours. The solvent was evaporated under reduce pressure and the residue was washed with water, acetone and ethyl acetate in turn to obtain the title compound 109 as a pale yellow solid (1.8 g, 64%): LCMS: 444 [M+1]$^+$.

Step 1h. Ethyl 2-(4-(6-(5-(2-chloro-6-methylphenylcarbamoyl)thiazol-2-ylamino)-2-methylpyrimidin-4-yl)piperazin-1-yl)acetate (Compound 110-1)

A mixture of compound 109 (0.31 g, 0.70 mmol), ethyl 2-bromoacetate (117 mg, 0.70 mmol), triethylamine (0.28 g, 0.70 mmol) and DMF (5 mL) was stirred at 35° C. for 2 minutes. The solvent was evaporated under reduce pressure to give the title compound 110-1 as a white solid (333 mg, 90%) which was used directly to the next step without further purification: LCMS: 530 [M+1]$^+$.

Step 1i. N-(2-Chloro-6-methylphenyl)-2-(6-(4-(2-(hydroxyamino)-2-oxoethyl)piperazin-1-yl)-2-methylpyrimidin-4-ylamino)thiazole-5-carboxamide (Compound 1)

To a stirred solution of hydroxylamine hydrochloride (4.67 g, 67.0 mmol) in methanol (24 mL) at 0° C. was added a solution of potassium hydroxide (5.61 g, 100.0 mmol) in methanol (14 mL). After addition, the mixture was stirred for 30 minutes at 0° C., and was allowed to stand at 0° C. The resulting precipitate was isolated, and the solution was prepared to give free hydroxylamine.

The above freshly prepared hydroxylamine solution (0.5 mL, 0.89 mmol) was placed in 5 mL flask. Compound 110-1 (333 mg, 0.63 mmol) was added to this solution under ultrasonic for 10 minutes. The reaction process was monitored by TLC. The mixture was neutralized with acetic acid and was then concentrated under reduce pressure. The residue was purified by preparative HPLC to give the title compound 1 as a white solid (50 mg, 16%): LCMS: 517 [M+1]$^+$; $^1$H NMR (DMSO-d$_6$) δ 2.20 (s, 3H), 2.38 (s, 3H), 2.58 (m, 4H), 2.90(s, 2H), 3.51(m, 4H), 6.02(s, 1H), 7.26(m, 2H), 7.37(m, 1H), 8.20(s, 1H), 8.80(s, 1H), 9.86(s, 1H), 10.47(s, 1H), 11.46(s, 1H).

Example 2

Preparation of N-(2-chloro-6-methylphenyl)-5-(6-(4-(3-(hydroxyamino)-3-oxopropyl)piperazin-1-yl)-2-methylpyrimidin-4-ylamino)-4H-pyrrole-3-carboxamide (Compound 2)

Step 2a. Methyl 3-(4-(6-(5-(2-chloro-6-methylphenylcarbamoyl)thiazol-2-ylamino)-2-methylpyrimidin-4-yl)piperazin-1-yl)propanoate (Compound 110-2)

The title compound 110-2 was prepared as a pale yellow solid (0.31 g, 74%) from compound 109 (0.35 g, 0.79 mmol), methyl 3-bromopropanoate (0.13 g, 0.78 mmol), DIEA (0.21 g, 1.58 mmol) and DMF (5 mL) using a procedure similar to that described for compound 110-1 (Example 1): LCMS: 530[M+1]$^+$.

Step 2b. N-(2-Chloro-6-methylphenyl)-2-(6-(4-(3-(hydroxyamino)-3-oxopropyl)piperazin-1-yl)-2-methylpyrimidin-4-ylamino)thiazole-5-carboxamide (Compound 2)

The title compound 2 was prepared as a white solid (60 mg, 19%) from compound 110-2 (0.31 g, 0.59 mmol) using a procedure similar to that described for compound 1 (Example 1): LCMS: 531 [M+1]$^-$; $^1$H NMR (DMSO-d$_6$) δ 2.16 (t, J=6.9 Hz, 2H), 2.24 (s, 3H), 2.41 (s, 3H), 2.54 (m, 4H), 2.57 (t, J=6.6 Hz, 2H), 3.50(m, 4H), 6.05 (s, 1H), 7.25 (m, 2H), 7.37 (m, 1H), 8.23 (s, 1H), 8.88 (s, 1H), 9.90 (s, 1H), 10.42 (s, 1H), 11.51 (s, 1H).

Example 3

Preparation of N-(2-chloro-6-methylphenyl)-2-(6-(4-(4-(hydroxyamino)-4-oxobutyl)piperazin-1-yl)-2-methylpyrimidin-4-ylamino)thiazole-5-carboxamide (Compound 3)

Step 3a. Ethyl 4-(4-(6-(5-(2-chloro-6-methylphenylcarbamoyl)thiazol-2-ylamino)-2-methylpyrimidin-4-yl)piperazin-1-yl)butanoate (Compound 110-3)

The title compound 110-3 was prepared as a pale yellow solid (0.22 g, 71%) from compound 109 (0.25 g, 0.56 mmol), ethyl 4-bromobutanoate (0.12 g, 0.56 mmol), DIEA (0.15 g, 0.56 mmol) and DMF (5 mL) using a procedure similar to that described for compound 110-1 (Example 1): LCMS: 558 $[M+1]^+$.

Step 3b. N-(2-chloro-6-methylphenyl)-2-(6-(4-(4-(hydroxyamino)-4-oxobutyl)piperazin-1-yl)-2-methylpyrimidin-4-ylamino)thiazole-5-carboxamide (Compound 3)

The title compound 3 was prepared as a white solid (30 mg, 14%) from compound 110-3 (0.22 g, 0.40 mmol) using a procedure similar to that described for compound 1 (Example 1): LCMS: 545 $[M+1]^-$; $^1$H NMR (DMSO-$d_6$) δ 1.69 (m, 2H), 2.01 (t, J=6.6 Hz, 2H), 2.25 (s, 3H), 2.30 (t, J=6.9 Hz, 2H), 2.41 (m, 4H), 2.55 (s, 3H), 3.52 (m, 4H), 6.06 (s, 1H), 7.25 (m, 2H), 7.36 (m, 1H), 8.23 (s, 1H), 8.70 (s, 1H), 9.90 (s, 1H), 10.37 (s, 1H), 11.50 (s, 1H).

Example 4

Preparation of N-(2-chloro-6-methylphenyl)-2-(6-(4-(5-(hydroxyamino)-5-oxopentyl)piperazin-1-yl)-2-methylpyrimidin-4-ylamino)thiazole-5-carboxamide (Compound 4)

Step 4a. Methyl methyl 5-(4-(6-(5-(2-chloro-6-methylphenylcarbamoyl)thiazol-2-ylamino)-2-methylpyrimidin-4-yl)piperazin-1-yl)pentanoate (Compound 110-4)

The title compound 110-4 was prepared as a pale yellow solid (120 mg, 39%) from compound 109 (0.24 g, 0.54 mmol), methyl 5-bromopentanoate (0.12g, 0.60 mmol), DIEA (1.54 g, 1.20 mmol) and DMF (3 mL) using a procedure similar to that described for compound 110-1 (Example 1): LCMS: 558 $[M+1]^+$.

Step 4b. N-(2-chloro-6-methylphenyl)-2-(6-(4-(5-(hydroxyamino)-5-oxopentyl)piperazin-1-yl)-2-methylpyrimidin-4-ylamino)thiazole-5-carboxamide (Compound 4)

The title compound 4 was prepared as a white solid (30 mg, 25%) from compound 110-4 (120 mg, 0.22 mmol) using a procedure similar to that described for compound 1 (Example 1): LCMS: 559 $[M+1]^-$; $^1$H NMR (DMSO-$d_6$) δ 1.44 (m, 4H), 1.95 (t, J=7.5 Hz, 2H), 2.22 (s, 3H), 2.26 (t, J=6.9 Hz, 2H), 2.37 (m, 7H), 3.47 (m, 4H), 6.07 (s, 1H), 7.25 (m, 2H), 7.37 (dd, J=2.1 Hz, J=7.2 Hz, 2H), 8.23(s, 1H), 9.93(s, 1H).

Example 5

Preparation of N-(2-chloro-6-methylphenyl)-2-(6-(4-(6-(hydroxyamino)-6-oxohexyl)piperazin-1-yl)-2-methylpyrimidin-4-ylamino)thiazole-5-carboxamide (Compound 5)

Step 5a. Ethyl 6-(4-(6-(5-(2-chloro-6-methylphenylcarbamoyl)thiazol-2-ylamino)-2-methylpyrimidin-4-yl)piperazin-1-yl)hexanoate (Compound 110-5)

The title compound 110-5 was prepared as a brown solid (120 mg, 41%) from compound 109 (0.22 g, 0.495 mol), ethyl 6-bromohexanoate (0.12 g, 0.495 mmol), potassium carbonate (0.22 g, 1.60 mmol) and DMF (5 mL) using a procedure similar to that described for compound 110-1 (Example 1): LCMS: 586 $[M+1]^+$.

Step 5b. N-(2-Chloro-6-methylphenyl)-2-(6-(4-(6-(hydroxyamino)-6-oxohexyl)piperazin-1-yl)-2-methylpyrimidin-4-ylamino)thiazole-5-carboxamide (Compound 5)

The title compound 5 was prepared as a white solid (30 mg, 26%) from compound 110-5 (120 mg, 0.20 mmol) using a procedure similar to that described for compound 1 (Example 1): LC-MS: 573 $[M+1]^+$; $^1$H NMR (DMSO-$d_6$) δ 1.26 (m, 2H), 1.49 (m, 4H), 1.93 (t, J=7.2 Hz, 2H), 2.22 (s, 3H), 2.26 (t, J=7.2 Hz, 2H), 2.48 (m, 7H), 3.47 (m, 4H), 6.04 (s, 1H), 7.26 (m, 2H), 7.37 (m, 2H), 8.21 (s, 1H), 8.66 (s, 1H), 9.88 (s, 1H), 10.33 (s, 1H), 10.33 (s, 1H).

Example 6

Preparation of N-(2-chloro-6-methylphenyl)-2-(6-(2-(2-(hydroxyamino)-2-oxoethylamino) ethylamino)-2-methylpyrimidin-4-ylamino)thiazole-5-carboxamide (Compound 7)

Step 6a. 2-(6-(2-Aminoethylamino)-2-methylpyrimidin-4-ylamino)-N-(2-chloro-6-methylphenyl)thiazole-5-carboxamide (Compound 201)

A solution of compound 108 (3.0 g, 7.6 mmol) in ethane-1,2-diamine (50 mL) was heated to 80° C. and stirred for 10 hours. The reaction was then concentrated under vacuum and the residue was partitioned between $H_2O$ and EtOAc. The EtOAc phase was separated, washed with brine, dried ($Na_2SO_4$) and concentrated under vacuum to yield the title compound 201 as a brown solid (1.3 g, 40%). LC-MS: 418 $[M+1]^+$, H-NMR (DMSO-$d_6$): δ 1.86 (s, 2H), 2.22 (s, 3H), 2.36 (s, 3H), 2.48 (t, J=6.0 Hz, 2H), 2.76 (t, J =6.0 Hz, 2H), 3.15 (s, 1H), 5.88 (s, 1H), 7.26 (m, 2H), 7.37 (dd, J=2.4, J=6.9 Hz, 1H), 8.19 (s, 1H), 9.83 (s, 1H).

Step 6b. Ethyl 2-(2-(6-(5-(2-chloro-6-methylphenylcarbamoyl)thiazol-2-ylamino)-2-methylpyrimidin-4-yl amino)ethylamino)acetate (Compound 202-7)

A solution of compound 201 (0.50 g, 1.2 mmol) in DMF (15 mL) was added ethyl 2-bromoacetate (0.2 g, 1.2 mmol) and $K_2CO_3$ (41 mg, 0.3 mmol). The reaction was stirred at 30° C. for 2 hours. The mixture was concentrated under vacuum and the residue was purified by column chromatograph to obtain title compound 202-7 as a pale yellow solid (110 mg, 22%): LC-MS: 504 $[M+1]^+$.

Step 6c. N-(2-Chloro-6-methylphenyl)-2-(6-(2-(2-(hydroxyamino)-2-oxoethylamino)ethylamino)-2-methylpyrimidin-4-ylamino)thiazole-5-carboxamide (Compound 7)

The title compound 7 was prepared as a pale yellow solid (42 mg, 37%) from compound 202-7 (110 mg, 0.29 mmol) using a procedure similar to that described for compound 1 (Example 1): LC-MS: 491 [M+1]$^+$, H-NMR (DMSO-d$_6$): δ 2.21 (s, 3H), 2.34 (s, 3H), 2.60 (t, J=6 Hz, 2H), 3.03 (s, 2H), 3.11 (t, J=5.7 Hz, 2H), 5.86 (s, 1H), 7.22 (m, 2H), 7.36 (dd, J = 2.1, J =7.2 Hz, 1H), 8.18 (s, 1H), 9.83 (s, 1H).

Example 7

Preparation of N-(2-chloro-6-methylphenyl)-2-(6-(4-(7-(hydroxyamino)-7-oxoheptyl) piperazin-1-yl)-2-methylpyrimidin-4-ylamino)thiazole-5-carboxamide (Compound 6)

Step 7a. ethyl 7-(4-(6-(5-(2-chloro-6-methylphenylcarbamoyl)thiazol-2-ylamino)-2-methylpyrimidin-4-yl)piperazin-1-yl)heptanoate (Compound 110-6)

The title compound 110-6 was prepared as a brown solid (176 mg, 59%) from compound 109 (0.22 g, 0.50 mmol), ethyl 7-bromoheptanoate (0.12 g, 0.506 mmol), diisopropylethylamine (0.13 g, 1.00 mmol) and DMF (5 mL) using a procedure similar to that described for compound 110-1 (Example 1): LCMS: 600 [M+1]$^+$.

Step 7b. N-(2-chloro-6-methylphenyl)-2-(6-(4-(6-(hydroxyamino)-7-oxoheptyl)piperazin-1-yl)-2-methylpyrimidin-4-ylamino)thiazole-5-carboxamide (Compound 6)

The title compound 6 was prepared as a white solid (32 mg, 82%) from compound 110-6 (40 mg, 0.067 mmol) using a procedure similar to that described for compound 1 (Example 1): LC-MS: 587 [M+1]$^+$; $^1$H NMR (DMSO-d$_6$) δ 1.24 (m, 4H), 1.44 (m, 4H), 1.92 (t, J=7.2 Hz, 2H), 2.22 (s, 3H), 2.26 (t, J=6.3 Hz, 2H), 2.38 (ds, 7H), 3.48 (m, 4H), 6.03 (s, 1H), 7.26 (m, 2H), 7.37 (m, 1H), 8.19 (s, 1H), 8.63 (ds, 1H), 9.83 (s, 1H), 10.28 (s, 1H), 11.43 (s, 1H).

Example 8

Preparation of N-(2-chloro-6-methylphenyl)-2-(6-(2-(3-(hydroxyamino)-3-oxopropylamino)ethylamino)-2-methylpyrimidin-4-ylamino)thiazole-5-carboxamide(Compound 8)

Step 8a. Methyl 3-(2-(6-(5-(2-chloro-6-methylphenylcarbamoyl)thiazol-2-ylamino)-2-methylpyrimidin-4-ylamino)ethylamino)propanoate(Compound 202-8)

The title compound 202-8 was prepared as a white solid (400 mg, 31%) from compound 201 (1.08 g, 2.6 mol), methyl 4-bromobutanoate (0.44 g, 2.6 mmol) and K$_2$CO$_3$ (0.44 mg, 5.2 mmol) using a procedure similar to that described for compound 202-7 (Example 6): LCMS 504 [M+1]$^+$.H-NMR ((DMSO-d$_6$): δ 2.22 (s, 3H), 2.38 (s, 3H), 2.64 (t, J=6.9 Hz, 2H), 2.93 (t, J=6.0 Hz, 2H), 3.03 (t, J=6.6 Hz, 2H), 3.61 (s, 3H), 7.26 (m, 3H), 7.39 (m, 1H), 8.22 (s, 1H), 9.88 (s, 1H).

Step 8b. N-(2-chloro-6-methylphenyl)-2-(6-(2-(3-(hydroxyamino)-3-oxopropylamino)ethylamino)-2-methylpyrimidin-4-ylamino)thiazole-5-carboxamide (Compound 8)

The title compound 8 was prepared as a off white solid (30 mg, 60%) from compound 202-8 (51 mg, 0.10 mmol) using a procedure similar to that described for compound 1 (Example 1): LCMS 505 [M+1]$^+$; $^1$H NMR (DMSO-d$_6$), δ 2.13 (t, J=6.9 Hz 2H), 2.22 (s, 3H), 2.36 (s, 3H), 2.70 (t, J=6.6 Hz, 2H), 2.77 (t, J=6.9 Hz, 2H), 5.87 (s, 1H), 7.21(m, 3H), 7.39 (m, 1H), 8.19 (s, 1H), 9.84 (s, 1H).

Example 9

Preparation of N-(2-chloro-6-methylphenyl)-2-(6-(2-(6-(hydroxyamino)-6-oxohexylamino)ethylamino)-2-methylpyrimidin-4-ylamino)thiazole-5-carboxamide(Compound 11)

Step 9a. Ethyl 6-(2-(6-(5-(2-chloro-6-methylphenylcarbamoyl)thiazol-2-ylamino)-2-methylpyrimidin-4-ylamino)ethylamino)hexanoate (Compound 202-11)

The title compound 202-11 was prepared as a pale yellow solid (100 mg, 17%) from compound 201 (0.50 g, 1.2 mol), ethyl ethyl 6-bromohexanoate (0.27 g, 1.2 mmol) and K$_2$CO$_3$ (41 mg, 0.3 mmol) using a procedure similar to that described for compound 202-7 (Example 6): H-NMR (CDCl$_3$): δ 1.24 (m, 5H), 1.41 (m, 2H), 1.57 (m, 2H), 2.23 (t, J=7.2 Hz, 2H),2.34 (s, 3H), 2.50 (s, 3H), 2.57 (t, J=5.7 Hz, 2H), 2.84 (t, J=5.7 Hz, 2H), 3.37 (m, 2H), 4.11 (q, J=7.2 Hz, 2H), 5.46 (ds, 1H), 5.70 (s, 1H), 7.16 (m, 1H), 7.29(m, 3H), 8.15 (s, 1H).

Step 9b. N-(2-chloro-6-methylphenyl)-2-(6-(2-(6-(hydroxyamino)-6-oxohexylamino)ethylamino)-2-methylpyrimidin-4-ylamino)thiazole-5-carboxamide (Compound 11)

The title compound 11 was prepared as a off white solid (34 mg, 33%) from compound 202-11 (100 mg, 0.18 mmol) using a procedure similar to that described for compound 1 (Example 1): LCMS 547 [M+1]$^+$; $^1$H NMR (DMSO-d$_6$), δ 1.25 (m, 2H), 1.47 (m, 4H), 1.95 (t, J=7.2 Hz 2H), 2.21 (s, 3H), 2.37 (s, 3H), 2.75 (t, J=6.9 Hz, 2H), 2.91(t, J=6.6 Hz, 2H), 3.42 (ds, 1H), 5.90 (s, 1H), 7.22 (m, 4H), 8.19 (s,1H), 9.8 (s,1H), 10.4 (ds, 1H).

Example 10

Preparation of N-(2-chloro-6-methylphenyl)-2-(6-(6-(hydroxyamino)-6-oxohexylamino)-2-methylpyrimidin-4-ylamino)thiazole-5-carboxamide (Compound 23)

Step 10a. Methyl6-(6-(5-(2-chloro-6-methylphenylcarbamoyl)thiazol-2-ylamino)-2-methylpyrimidin-4-ylamino)hexanoate (Compound 301-23)

A solution of compound 108 (240 mg, 0.61 mmol), DMAC (15 mL), KOH (170 mg, 3.05 mmol) and methyl 6-aminohexanoate (554 mg, 3.05 mmol) was stirred for 12 h at 120° C. The reaction mixture was diluted with water, filtered and dried to give the crude compound 301-23 as a pale yellow powder (88 mg, 30%) which was used directly to next step without further purification. LCMS: 503 [M+1]$^+$.

Step 10b. N-(2-chloro-6-methylphenyl)-2-(6-(6-(hydroxyamino)-6-oxohexylamino)-2-methylpyrimidin-4-ylamino)thiazole-5-carboxamide (Compound 23)

A mixture of compound 301-23 (88 mg, 0.18 mmol) and freshly prepared NH$_2$OH methanol solution (1.77 M, 2.10 mL) was stirred for 30 min at room temperature. The mixture was adjusted to pH=7.0 with AcOH and the solvent was removed. The resulting residue was purified by column chromatography to give the title compound 23 as a white powder (25 mg, 29%): LCMS: 504 [M+1]$^+$; $^1$H NMR (DMSO-d$_6$) δ 11.30 (s, 1H), 10.29 (s, 1H), 9.80 (s, 1H), 8.60 (s, 1H), 8.17 (s, 1H), 7.38 (dd, 1H, J=2.1, J=7.2 Hz), 7.25 (m, 2H), 7.12 (m, 1H), 5.83 (s, 1H), 3.13 (brs, 2H), 2.34 (s, 3H), 2.22 (s, 3H), 1.93 (m, 2H), 1.50 (m, 1H), 1.26 (m, 2H).

Example 11

Preparation of N-(2-chloro-6-methylphenyl)-2-(6-(7-(hydroxyamino)-7-oxoheptylamino)-2-methylpyrimidin-4-ylamino)thiazole-5-carboxamide (Compound 24)

Step 11a. Methyl 7-(6-(5-(2-chloro-6-methylphenylcarbamoyl)thiazol-2-ylamino)-2-methylpyrimidin-4-ylamino)heptanoate (Compound 301-24)

The title compound 301-24 was prepared as a crude pale yellow solid (120 mg, 38%) from compound 108 (240 mg, 0.61 mmol), DMAC (15 mL), KOH (170 mg, 3.05 mmol) and methyl 7-aminoheptanoate (596 mg, 3.05 mmol) using a procedure similar to that described for compound 301-23 (Example 10): LCMS: 517 [M+1]$^+$.

Step 11b. N-(2-chloro-6-methylphenyl)-2-(6-(7-(hydroxyamino)-7-oxoheptylamino)-2-methylpyrimidin-4-ylamino)thiazole-5-carboxamide (Compound 24)

The title compound 24 was prepared as a white solid (35 mg, 30%) from compound 301-24 (120 mg, 0.23 mmol) and freshly prepared hydroxylamine methanol solution (1.77 M, 3.28 mL) using a procedure similar to that described for compound 23 (Example 10): m.p. 150.7° C. (decomp.), LCMS: 518 [M+1]$^+$; $^1$H NMR (DMSO-d$_6$) δ 11.37 (s, 1H), 10.33 (s, 1H), 9.85 (s, 1H), 8.66 (s, 1H), 8.18 (s, 1H), 7.39 (dd, 1H, J=2.1, J=7.2 Hz), 7.26 (m, 2H), 7.19 (m, 1H), 5.82 (s, 1H), 3.14 (brs, 2H), 2.34 (s, 3H), 2.22 (s, 3H), 1.92 (m, 2H), 1.47 (m, 4H), 1.27 (m, 4H).

Biological Assays:

As stated hereinbefore the derivatives defined in the present invention possess anti-proliferation activity. These properties may be assessed, for example, using one of the procedures set out below:

(a) An In Vitro Assay which Determines the Ability of a Test Compound to Inhibit a Tyrosine Kinase.

The ability of compounds to inhibit tyrosine kinase (Abl1, Src, c-Kit, and PDGFR-beta) activity is assayed using HTSCAN™ Receptor Kinase Assay Kits (Cell Signaling Technologies, Danvers, Mass.). Abl1 tyrosine kinase is obtained in partially purified form from GST-kinase fusion protein which is produced using a baculovirus expression system from a construct expressing human Abl1 (Pro118-Ser553) (GenBank Accession No. NM_005157) with an amino-terminal GST tag. Src tyrosine kinase is obtained in partially purified form from GST-kinase fusion protein which is produced using a baculovirus expression system from a construct expressing full length human Src (Met1-Leu536) (GenBank Accession No. NM_005417) with an amino-terminal GST tag. c-Kit tyrosine kinase is obtained in partially purified form from GST-kinase fusion protein which is produced using a baculovirus expression system from a construct expressing human c-Kit (Thr544-Val976) with an amino-terminal GST tag. PDGFR-beta tyrosine kinase was produced using a baculovirus expression system from a construct containing a human PDGFR-beta c-DNA (GenBank Accession No. NM_002609) fragment (Arg561-Leu1106) amino-terminally fused to a GST-HIS6-Thrombin cleavage site. The proteins are purified by one-step affinity chromatography using glutathione-agarose. An anti-phosphotyrosine monoclonal antibody, P-Tyr-100, is used to detect phosphorylation of biotinylated substrate peptides (Abl1 and Src, Biotin-Signal Transduction Protein (Tyr160); c-Kit, Biotinylated-KDR (Tyr996); PDGFR-β, Biotinylated-FLT3 (Tyr589)). Enzymatic activity is tested in 60 mM HEPES, 5 mM MgCl2 5 mM MnCl2 200 μM ATP, 1.25 mM DTT, 3 μM Na3VO4, 1.5 mM peptide, and 50 ng EGF Recpetor Kinase. Bound antibody is detected using the DELFIA system (PerkinElmer, Wellesley, Mass.) consisting of DELFIA® Europium-labeled Anti-mouse IgG (PerkinElmer, #AD0124), DELFIA® Enhancement Solution (PerkinElmer, #1244-105), and a DELFIA® Streptavidin coated, 96-well Plate (PerkinElmer, AAAND-0005). Fluorescence is measured on a WALLAC Victor 2 plate reader and reported as relative fluorescence units (RFU). Data are plotted using GraphPad Prism (v4.0a) and IC50's are calculated using a sigmoidal dose response curve fitting algorithm.

Test compounds are dissolved in dimethylsulphoxide (DMSO) to give a 20 mM working stock concentration. Each assay is setup as follows: 100 μl of 10 mM ATP is added to 1.25 ml 6 mM substrate peptide. The mixture is diluted with dH$_2$0 to 2.5 ml to make 2× ATP/substrate cocktail ([ATP]= 400 mM, [substrate]=3 mM). The enzyme is immediately transferred from −80° C. to ice. The enzyme is allowed to thaw on ice. The mixture is microcentrifuged briefly at 4° C. to bring liquid to the bottom of the vial and returned immediately to ice. 10 μl of DTT (1.25 mM) is added to 2.5 ml of 4× HTScan™ Tyrosine Kinase Buffer (240 mM HEPES pH 7.5, 20 mM MgCl$_2$, 20 mM MnCl, 12 mM NaVO$_3$) to make DTT/Kinase buffer. 1.25 ml of DTT/Kinase buffer is transferred to enzyme tube to make a 4× reaction cocktail ([enzyme]=4 ng/μL in 4× reaction cocktail). 12.5 μl of the 4× reaction cocktail is incubated with 12.5 μl/well of prediluted compound of interest (usually around 10 μM) for 5 minutes at room temperature. 25 μl of 2× ATP/substrate cocktail is added to 25 μl/well preincubated reaction cocktail/compound. The reaction plate is incubated at room temperature for 30 minutes. 50 μl/well Stop Buffer (50 mM EDTA, pH 8) is added to stop the reaction. 25 μl of each reaction and 75 μl dH$_2$O/well is transferred to a 96-well streptavidin-coated plate and incubated at room temperature for 60 minutes. The plate is washed three times with 200 μl/well PBS/T (PBS, 0.05% Tween-20). The primary antibody, Phospho-Tyrosine mAb (P-Tyr-100), is diluted 1:1000 in PBS/T with 1% bovine serum albumin (BSA). 100 μl/well primary antibody is added and the mixture is incubated at room temperature for 60 minutes. The plates are again washed three times with 200 μl/well PBS/T. Europium labeled anti-mouse IgG is diluted 1:500 in PBS/T with 1% BSA. 100 μl/well diluted antibody is added and the mixture is incubated at room temperature for 30 minutes. The plate is washed five times with 200 μl/well PBS/T. 100 μl/well DELFIA® Enhancement Solution is added and the mixture is incubated at room temperature for 5 minutes. 615 nm fluorescence emission is detected using an appropriate Time-Resolved Plate Reader.

(b) An In Vitro Assay which Determines the Ability of a Test Compound to Inhibit HDAC Enzymatic Activity.

HDAC inhibitors is screened using an HDAC fluorimetric assay kit (AK-500, Biomol, Plymouth Meeting, Pa.). Test compounds are dissolved in dimethylsulphoxide (DMSO) to give a 20 mM working stock concentration. Fluorescence is measured on a WALLAC Victor 2 plate reader and reported as relative fluorescence units (RFU). Data are plotted using GraphPad Prism (v4.0a) and IC50's calculated using a sigmoidal dose response curve fitting algorithm.

Each assay is setup as follows: Defrost all kit components and kept on ice until use. Dilute HeLa nuclear extract 1:29 in Assay Buffer (50 mM Tris/Cl, pH 8.0, 137 mM NaCl, 2.7 mM KCl, 1 mM MgCl2). Prepare dilutions of Trichostatin A (TSA, positive control) and tested compounds in assay buffer (5× of final concentration). Dilute Fluor de Lys™ Substrate in assay buffer to 100 uM (50 fold=2× final). Dilute Fluor de Lys™ developer concentrate 20-fold (e.g. 50 μl plus 950 μl Assay Buffer) in cold assay buffer. Second, dilute the 0.2 mM Trichostatin A 100-fold in the 1× Developer (e.g. 10 μl in 1 ml; final Trichostatin A concentration in the 1× Developer=2 μM; final concentration after addition to HDAC/Substrate reaction=1 μM). Add Assay buffer, dilute trichostatin A or test inhibitor to appropriate wells of the microtiter plate. Add diluted HeLa extract or other HDAC sample to all wells except for negative controls. Allow diluted Fluor de Lys™ Substrate and the samples in the microtiter plate to equilibrate to assay temperature (e.g. 25 or 37° C. Initiate HDAC reactions by adding diluted substrate (25 μl) to each well and mixing thoroughly. Allow HDAC reactions to proceed for 1 hour and then stopped them by addition of Fluor de Lys™ Developer (50 μl). Incubate plate at room temperature (25° C.) for 10-15 min. Read samples in a microtiter-plate reading fluorimeter capable of excitation at a wavelength in the range 350-380 nm and detection of emitted light in the range 440-460 nm.

The following TABLE B lists compounds representative of the invention and their activity in HDAC,SRC,c-Kit, PDGF and ABL assays. In these assays, the following grading was used: I≧10 μM, 10 μM>II>1 μM, 1 μM>III>0.1 μM, and IV≦0.1 μM for IC$_{50}$.

TABLE B

| Compound No. | HDAC | ABL | SRC | c-Kit | PDGFb | Lyn | Lck |
|---|---|---|---|---|---|---|---|
| 1 | II | IV | IV | | IV | | |
| 2 | II | IV | IV | | IV | | |
| 3 | II | IV | IV | | | | |
| 4 | III | IV | IV | | IV | | |
| 5 | IV | IV | IV | IV | IV | IV | |
| 6 | III | IV | IV | IV | IV | IV | |
| 7 | I | IV | IV | | | | |
| 11 | IV | IV | IV | IV | IV | IV | IV |
| 23 | IV | IV | IV | IV | IV | IV | IV |
| 24 | IV | IV | IV | IV | IV | IV | IV |
| 30 | I | III | III | | | | |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a cancer which is susceptible to inhibition of one or more of Src, BCR-ABL and HDAC, in a subject in need thereof, the method comprising administering to the subject a therapeutically effective amount of a compound represented by formula (I) or (II):

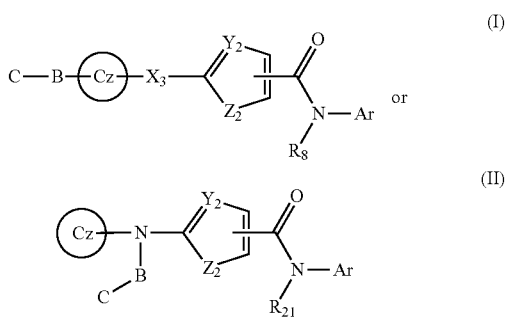

or a pharmaceutically acceptable salt, or solvate thereof, wherein

Cz is pyrimidine or substituted pyrimidine;

Ar is aryl, substituted aryl heteroaryl or substituted heteroaryl;

$X_3$ is NH, alkylamino, O or S;

$Z_2$ is O, S, NH or alkylamino;

$Y_2$ is N or $CR_{20}$; where $R_{20}$ is selected from hydrogen, halogen, aliphatic, substituted aliphatic, aryl, substituted aryl, heteroaryl, substituted heteroaryl;

$R_{21}$ is hydrogen or aliphatic;

B is a direct bond or straight- or branched-, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocycloalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylherreroaryl, in which one or more methylenes can be interrupted or terminated by O S, S(O), $SO_2$, N($R_8$), C(O), substituted or unsubstituted aryl, substituted or unsubstituted heteroaryl, substituted or unsubstituted heterocyclic; where $R_8$ is hydrogen, acyl, aliphatic or substituted aliphatic;

C is selected from:

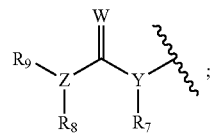
(a)

where W is O or S; Y is absent, N, or CH; Z is N or CH; $R_7$ and $R_9$ are independently hydrogen, OR', aliphatic or substituted aliphatic, wherein R' is hydrogen, aliphatic, substituted aliphatic or acyl; provided that if $R_7$ and $R_9$ are both present, one of $R_7$ or $R_9$ must be OR' and if Y is absent, $R_9$ must be OR'; and $R_{21}$ is hydrogen, acyl, aliphatic, or substituted aliphatic;

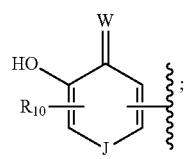
(b)

where W is O or S; J is O, NH or $NCH_3$; and $R_{10}$ is hydrogen or lower alkyl;

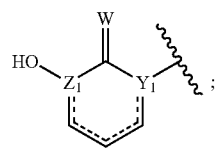
(c)

where W is O or S; $Y_1$ and $Z_1$ are independently N, C or CH; and

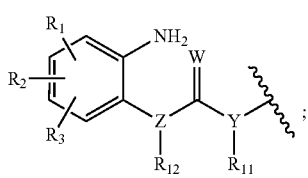
(d)

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $N_3$, $NO_2$, sulfonyl, acyl, aliphatic, substituted aliphatic, aryl, substituted aryl, heteroaryl, substituted heteroaryl, heterocyclic, and substituted heterocyclic.

2. The method of claim 1, wherein the compound of Formula I is represented by formula (III):

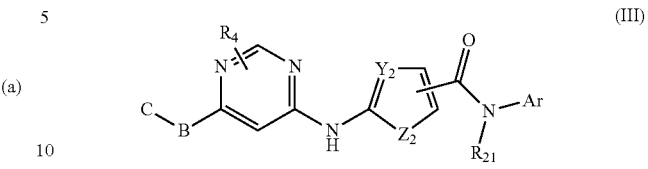
(III)

wherein $R_4$ is hydrogen, aliphatic or substituted aliphatic; and C, B, $Y_2$, $Z_2$, Ar and $R_{21}$ are as previously defined in claim 1.

3. The method of claim 1, wherein the compound of Formula I is represented by formula (IV):

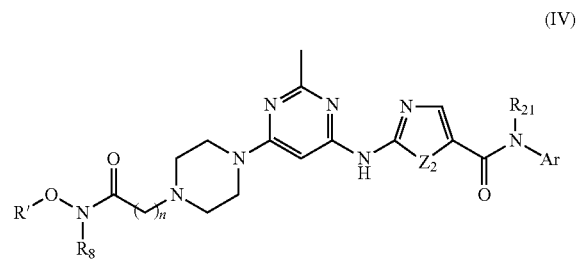
(IV)

wherein n is 1-9; and R', $Z_2$, Ar and $R_{21}$ are as previously defined in claim 1.

4. The method of claim 1, wherein the compound of Formula I is represented by formula (V):

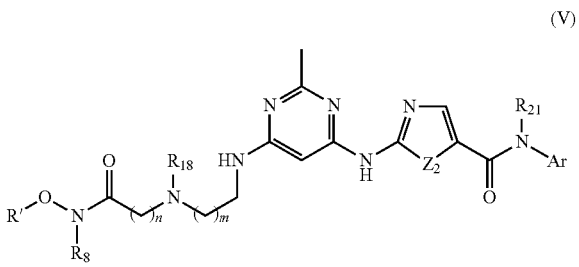
(V)

wherein m and n are independently 1-9; $R_{18}$ is independently $R_8$; and R', $Z_2$, Ar, $R_8$, and $R_{21}$ are as previously defined in claim 1.

5. The method of claim 1, wherein the compound of Formula I is represented by formula (VI):

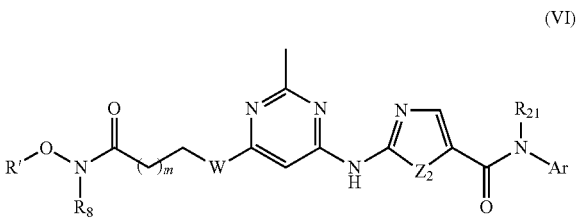
(VI)

wherein m is 0-9; W is O, NH, alkylamino, S, SO, or $SO_2$; and $Z_2$, Ar, R', $R_8$, and $R_{21}$ are as previously defined in claim 1.

6. The method of claim 1, wherein the compound of is represented by formula (VII):

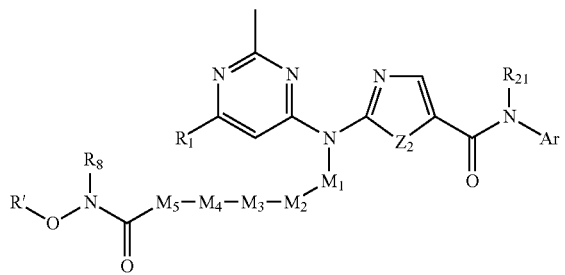

(VII)

wherein $M_1$ is absent, O, NH, alkylamino, $C_1$-$C_6$ alkyl, $C_2$-$C_6$ alkenyl, or $C_2$-$C_6$ alkynyl; $M_2$ is absent, $C_1$-$C_6$ alkyl, O, NH, alkylamine, S, SO, $SO_2$, heterocyclic, heteroaryl, aryl, or C=O; $M_3$ is absent, O, NH, alkylamino, C=O, $C_1$-$C_6$ alkyl, $C_2$-$C_6$ alkenyl, or $C_2$-$C_6$ alkynyl; $M_4$ is absent, O, NH, alkylamino, heterocyclic, heteroaryl or aryl; $M_5$ is absent, $C_1$-$C_8$ alkyl, $C_2$-$C_8$ alkenyl, $C_2$-$C_8$ alkynyl, heterocyclic, heteroaryl or aryl; R' is hydrogen, aliphatic, substituted aliphatic or acyl; $R_1$ is selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $N_3$, $NO_2$, sulfonyl, acyl, aliphatic, substituted aliphatic, aryl, substituted aryl, heteroaryl, substituted heteroaryl, heterocyclic, and substituted heterocyclic; $Z_2$ is O, S, NH or alkylamino;

Ar is aryl, substituted aryl, heteroaryl or substituted heteroaryl; and $R_{21}$ is hydrogen or aliphatic.

7. A method of treating a cancer which is susceptible to inhibition of one or more of Src, Bcr-Abl and HDAC, in a subject in need thereof, the method comprising administering to the subject a therapeutically effective amount of a compound represented by formula (VIII):

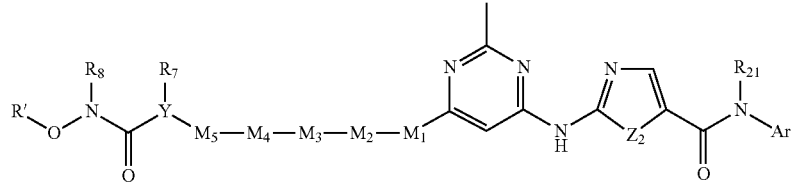

(VIII)

wherein $M_1$ is absent, O,NH, alkylamino, $C_1$-$C_6$ alkyl, $C_2$-$C_6$ alkenyl, $C_2$-$C_6$ alkynyl; $M_2$ is absent, $C_1C_6$ alkyl, $C_2$-$C_6$ alkenyl, $C_2$-$C_6$, O,NH, alkylamine, S, SO, $SO_2$, heterocyclic, heteroaryl, aryl or C=O; $M_3$ is absent, O, NH, alkylamino, S, SO, $SO_2$, $C_1$-$C_6$ alkyl, $C_2$-$C_6$ alkenyl, $C_2$-$C_6$ alkynyl, heterocyclic, heteroaryl, aryl or C=O; $M_4$ is absent, O, NH, alkylamino, CO, S, SO, $SO_2$, heterocyclic, heteroaryl or aryl; $M_5$ is absent, $C_1C_6$ alkyl, $C_2$-$C_6$ alkenyl, $C_2$-$C_6$ alkynyl, heterocyclic, heteroaryl or aryl; R' is hydrogen, aliphatic, substituted aliphatic or acyl; $Z_2$ is O, S, NH or alkylamino; Ar is aryl, substituted aryl, heteroaryl or substituted heteroaryl; Y is absent, N or CH; $R_7$ is hydrogen, aliphatic or substituted aliphatic; $R_8$ is H or aliphatic; and $R_{21}$ is hydrogen or aliphatic.

8. The method of claim 1, wherein the compound of Formula I or Formula II is selected from the compounds delineated in Table A or a pharmaceutically acceptable salt or solvate thereof:

TABLE A

| Compound # | Structure |
| --- | --- |
| 1 | 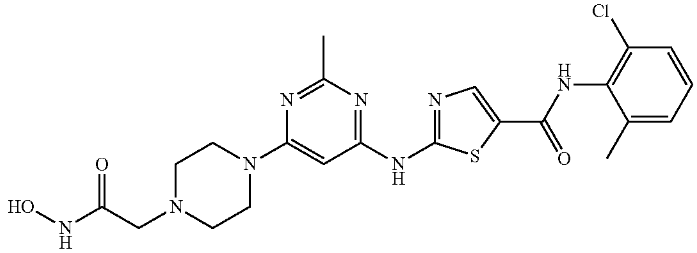 [SMILES: Cc1nc(Nc2ncc(C(=O)Nc3c(C)cccc3Cl)s2)cc(N2CCN(CC(=O)NO)CC2)n1] |

TABLE A-continued

| Compound # | Structure |
|---|---|
| 2 | 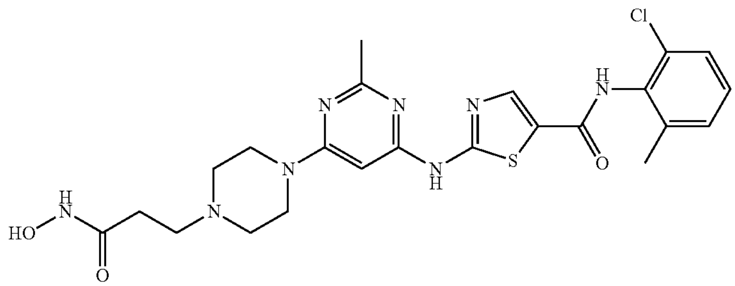 [SMILES: Cc1nc(Nc2ncc(C(=O)Nc3c(C)cccc3Cl)s2)cc(N2CCN(CCC(=O)NO)CC2)n1] |
| 3 | 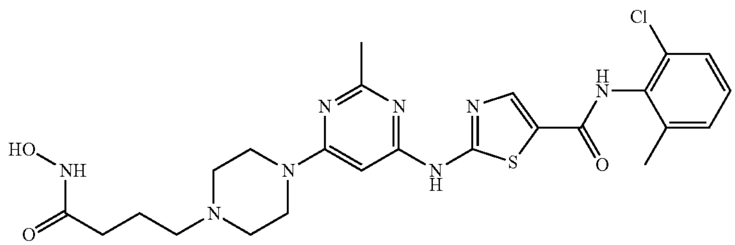 [SMILES: Cc1nc(Nc2ncc(C(=O)Nc3c(C)cccc3Cl)s2)cc(N2CCN(CCCC(=O)NO)CC2)n1] |
| 4 | 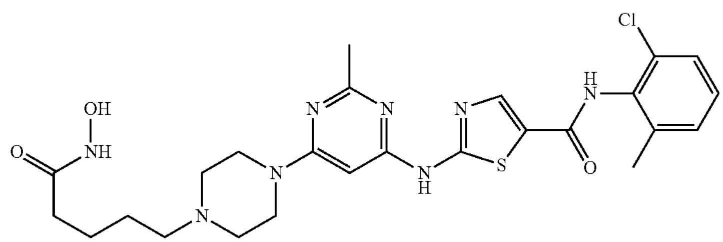 [SMILES: Cc1nc(Nc2ncc(C(=O)Nc3c(C)cccc3Cl)s2)cc(N2CCN(CCCCC(=O)NO)CC2)n1] |
| 5 | 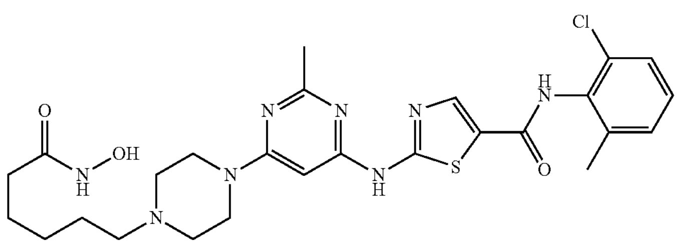 [SMILES: Cc1nc(Nc2ncc(C(=O)Nc3c(C)cccc3Cl)s2)cc(N2CCN(CCCCCC(=O)NO)CC2)n1] |
| 6 | 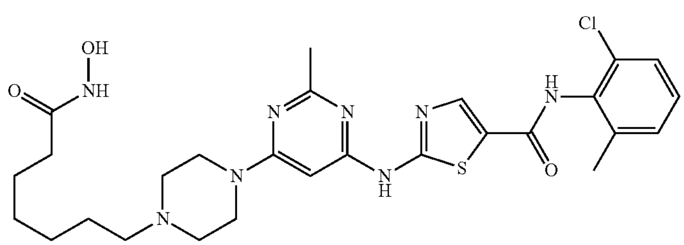 [SMILES: Cc1nc(Nc2ncc(C(=O)Nc3c(C)cccc3Cl)s2)cc(N2CCN(CCCCCCC(=O)NO)CC2)n1] |
| 7 | 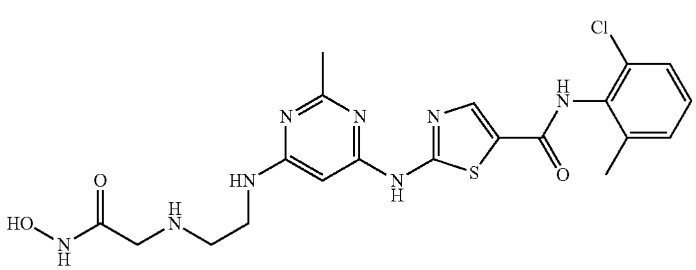 |

TABLE A-continued

| Compound # | Structure |
| --- | --- |
| 8 | 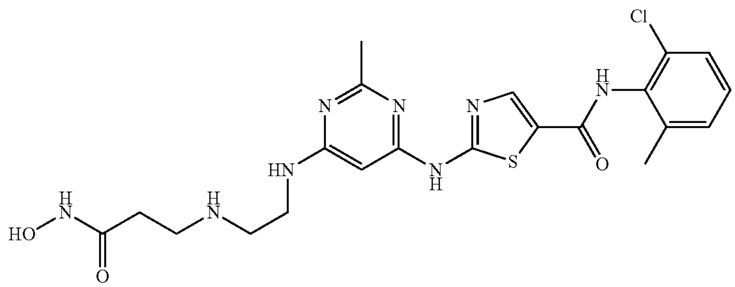 [SMILES: Cc1nc(NCCNCCC(=O)NO)cc(Nc2ncc(C(=O)Nc3c(C)cccc3Cl)s2)n1] |
| 9 | 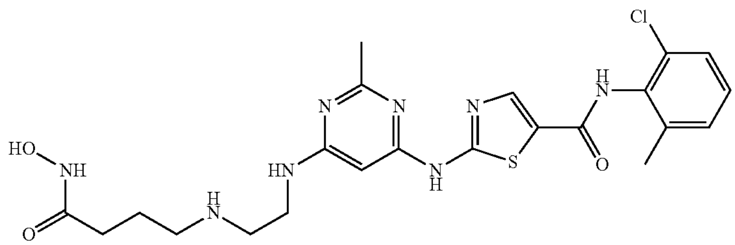 [SMILES: Cc1nc(NCCNCCCC(=O)NO)cc(Nc2ncc(C(=O)Nc3c(C)cccc3Cl)s2)n1] |
| 10 | 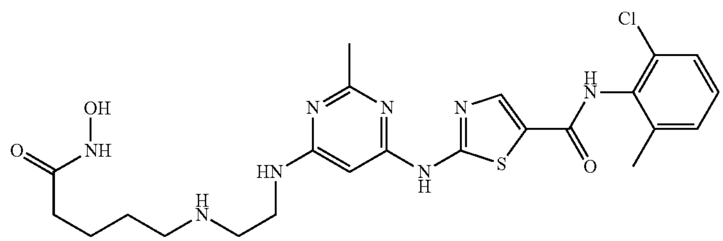 [SMILES: Cc1nc(NCCNCCCCC(=O)NO)cc(Nc2ncc(C(=O)Nc3c(C)cccc3Cl)s2)n1] |
| 11 | 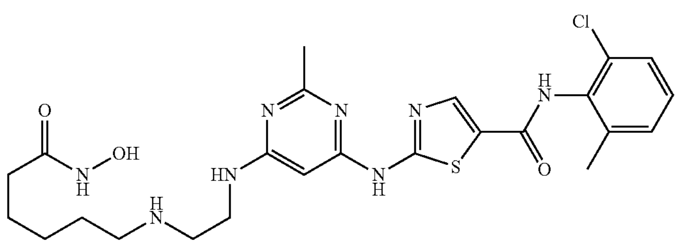 |
| 12 | 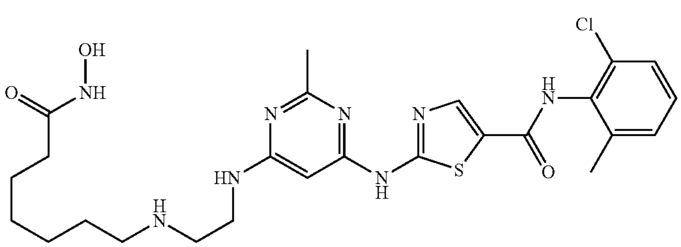 [SMILES: Cc1nc(NCCNCCCCCCC(=O)NO)cc(Nc2ncc(C(=O)Nc3c(C)cccc3Cl)s2)n1] |
| 13 | 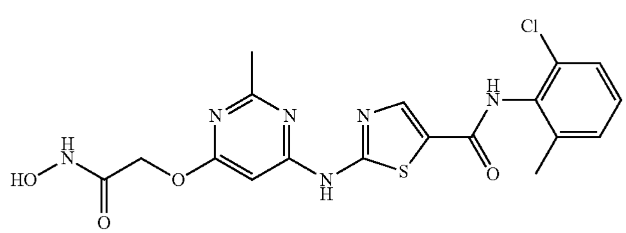 [SMILES: Cc1nc(Nc2ncc(C(=O)Nc3c(C)cccc3Cl)s2)cc(OCC(=O)NO)n1] |

TABLE A-continued

| Compound # | Structure |
|---|---|
| 14 | 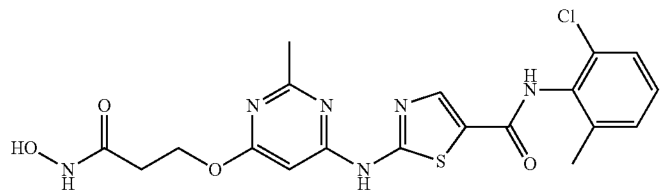 [SMILES: Cc1nc(Nc2ncc(C(=O)Nc3c(C)cccc3Cl)s2)cc(OCCC(=O)NO)n1] |
| 15 | 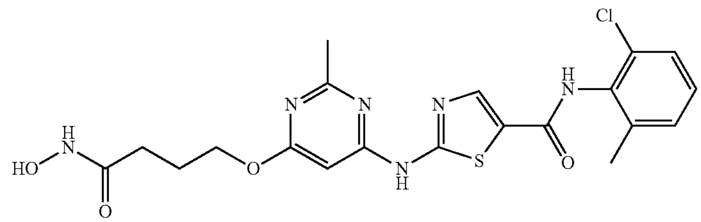 [SMILES: Cc1nc(Nc2ncc(C(=O)Nc3c(C)cccc3Cl)s2)cc(OCCCC(=O)NO)n1] |
| 16 | 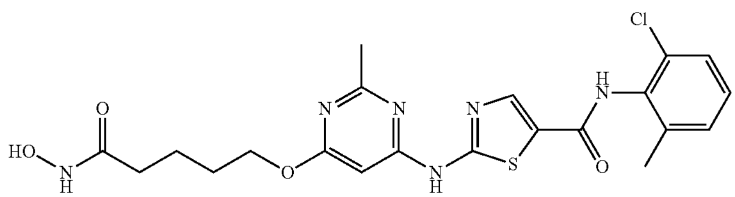 [SMILES: Cc1nc(Nc2ncc(C(=O)Nc3c(C)cccc3Cl)s2)cc(OCCCCC(=O)NO)n1] |
| 17 | 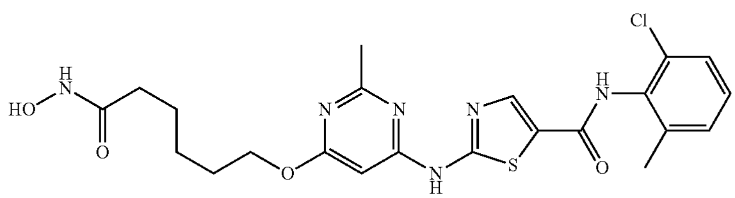 [SMILES: Cc1nc(Nc2ncc(C(=O)Nc3c(C)cccc3Cl)s2)cc(OCCCCCC(=O)NO)n1] |
| 18 | 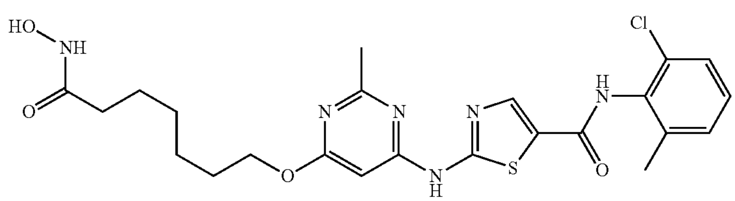 [SMILES: Cc1nc(Nc2ncc(C(=O)Nc3c(C)cccc3Cl)s2)cc(OCCCCCCC(=O)NO)n1] |
| 19 | 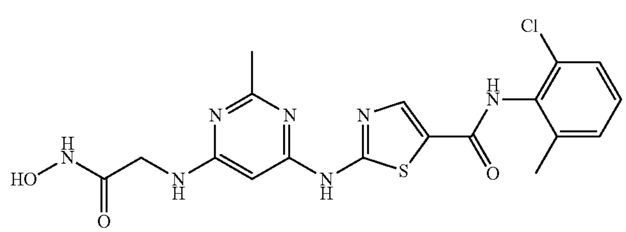 |
| 20 | 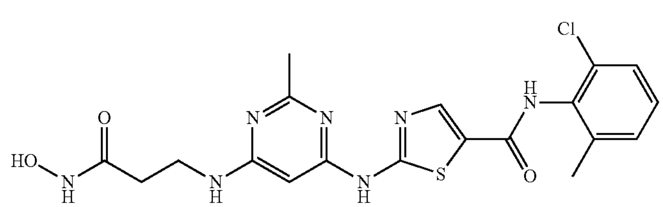 [SMILES: Cc1nc(NCCC(=O)NO)cc(Nc2ncc(C(=O)Nc3c(C)cccc3Cl)s2)n1] |

TABLE A-continued
| Compound # | Structure |
|---|---|
| 21 | 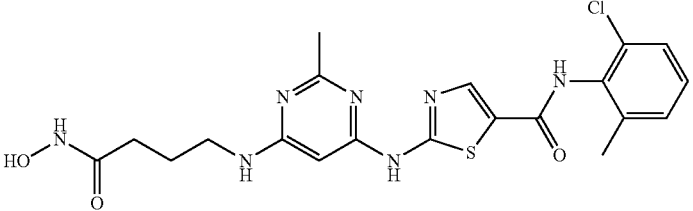 [SMILES: Cc1nc(NCCCC(=O)NO)cc(Nc2ncc(C(=O)Nc3c(C)cccc3Cl)s2)n1] |
| 22 | 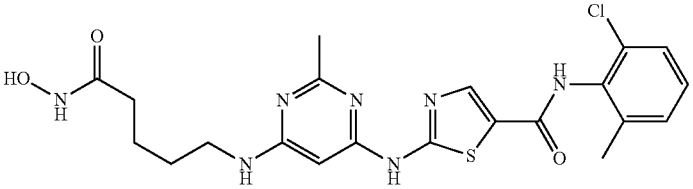 [SMILES: Cc1nc(NCCCCC(=O)NO)cc(Nc2ncc(C(=O)Nc3c(C)cccc3Cl)s2)n1] |
| 23 | 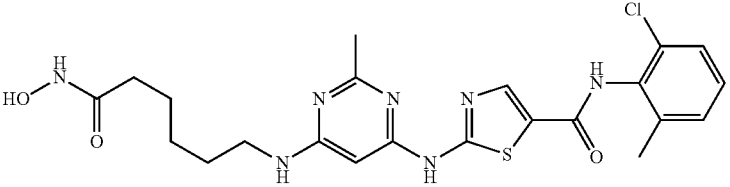 [SMILES: Cc1nc(NCCCCCC(=O)NO)cc(Nc2ncc(C(=O)Nc3c(C)cccc3Cl)s2)n1] |
| 24 | 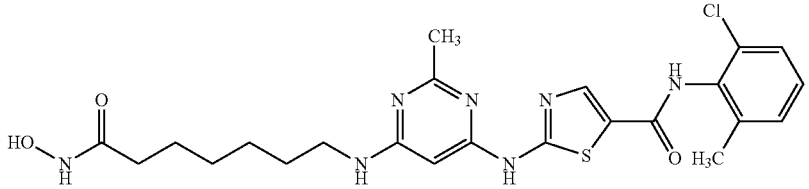 [SMILES: Cc1nc(NCCCCCCC(=O)NO)cc(Nc2ncc(C(=O)Nc3c(C)cccc3Cl)s2)n1] |
| 25 | 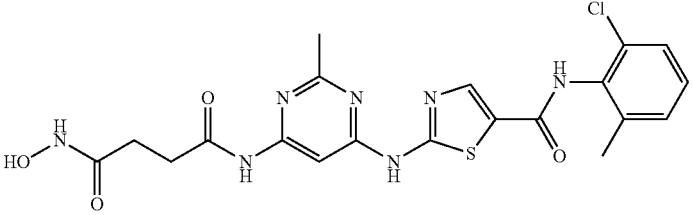 [SMILES: Cc1nc(NC(=O)CCC(=O)NO)cc(Nc2ncc(C(=O)Nc3c(C)cccc3Cl)s2)n1] |
| 26 | 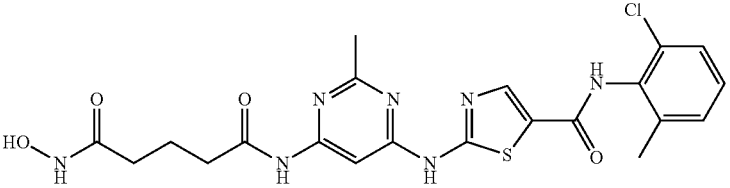 [SMILES: Cc1nc(NC(=O)CCCC(=O)NO)cc(Nc2ncc(C(=O)Nc3c(C)cccc3Cl)s2)n1] |
| 27 | 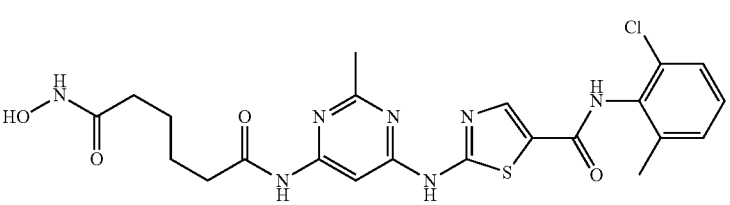 [SMILES: Cc1nc(NC(=O)CCCCC(=O)NO)cc(Nc2ncc(C(=O)Nc3c(C)cccc3Cl)s2)n1] |

TABLE A-continued

| Compound # | Structure |
|---|---|
| 28 | 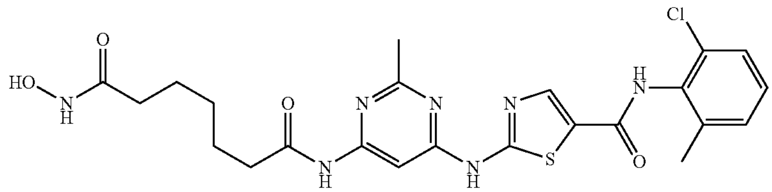 [SMILES: Cc1nc(NC(=O)CCCCCC(=O)NO)cc(Nc2ncc(C(=O)Nc3c(C)cccc3Cl)s2)n1] |
| 29 | 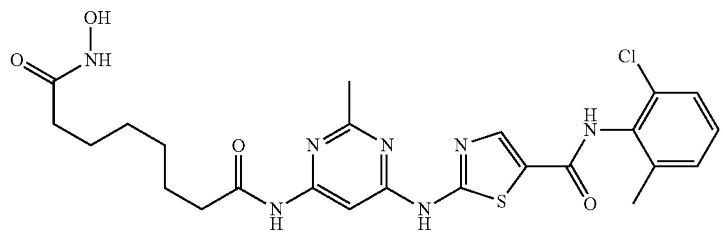 [SMILES: Cc1nc(NC(=O)CCCCCCC(=O)NO)cc(Nc2ncc(C(=O)Nc3c(C)cccc3Cl)s2)n1] |
| 30 | 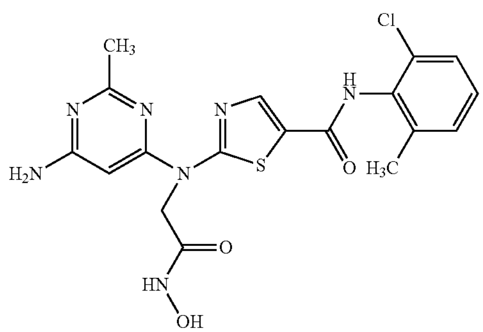 [SMILES: Cc1nc(N)cc(N(CC(=O)NO)c2ncc(C(=O)Nc3c(C)cccc3Cl)s2)n1] |
| 31 | 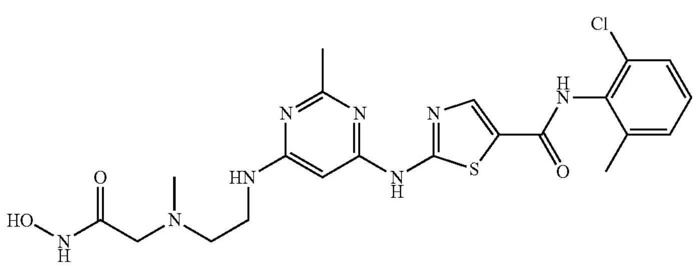 [SMILES: Cc1nc(NCCN(C)CC(=O)NO)cc(Nc2ncc(C(=O)Nc3c(C)cccc3Cl)s2)n1] |
| 32 | 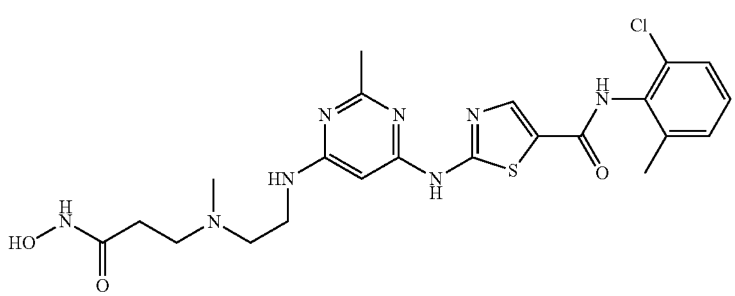 [SMILES: Cc1nc(NCCN(C)CCC(=O)NO)cc(Nc2ncc(C(=O)Nc3c(C)cccc3Cl)s2)n1] |
| 33 | 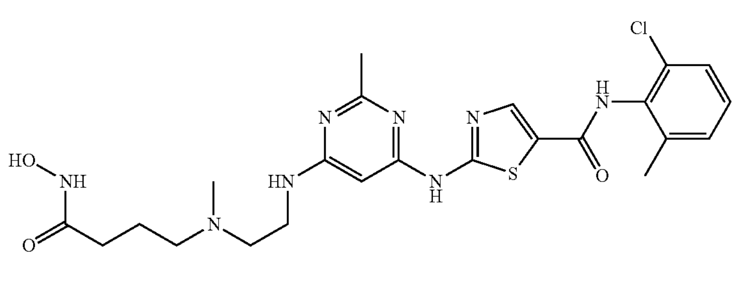 [SMILES: Cc1nc(NCCN(C)CCCC(=O)NO)cc(Nc2ncc(C(=O)Nc3c(C)cccc3Cl)s2)n1] |

TABLE A-continued

| Compound # | Structure |
|---|---|
| 34 | 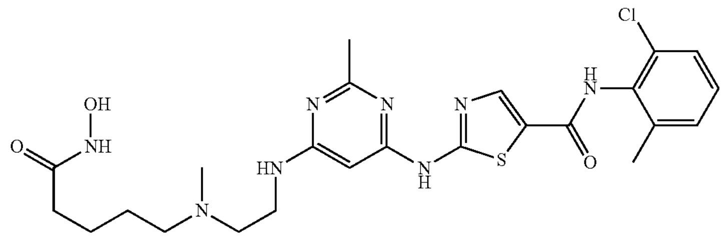 [SMILES: Cc1nc(NCCN(C)CCCCC(=O)NO)cc(Nc2ncc(C(=O)Nc3c(C)cccc3Cl)s2)n1] |
| 35 | 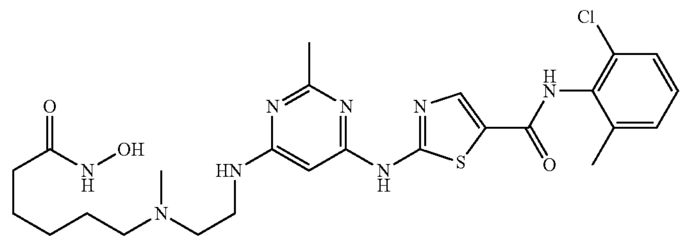 [SMILES: Cc1nc(NCCN(C)CCCCCC(=O)NO)cc(Nc2ncc(C(=O)Nc3c(C)cccc3Cl)s2)n1] |
| 36 | 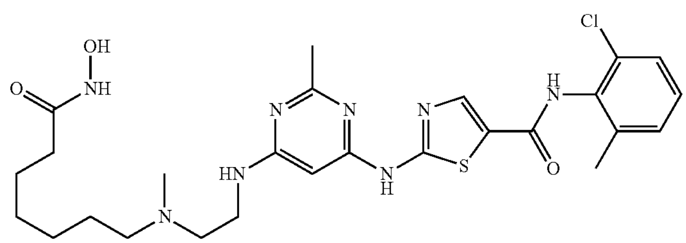 [SMILES: Cc1nc(NCCN(C)CCCCCCC(=O)NO)cc(Nc2ncc(C(=O)Nc3c(C)cccc3Cl)s2)n1] |
| 37 | 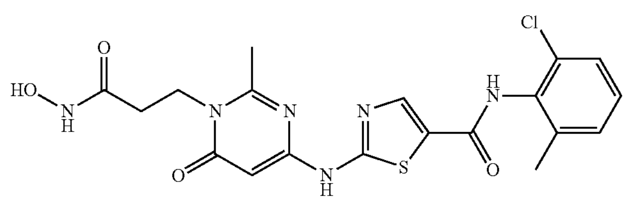 [SMILES: Cc1cccc(Cl)c1NC(=O)c1cnc(Nc2cc(=O)n(CCC(=O)NO)c(C)n2)s1] |
| 38 | 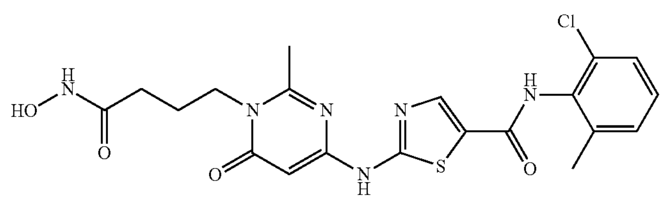 [SMILES: Cc1cccc(Cl)c1NC(=O)c1cnc(Nc2cc(=O)n(CCCC(=O)NO)c(C)n2)s1] |
| 39 | 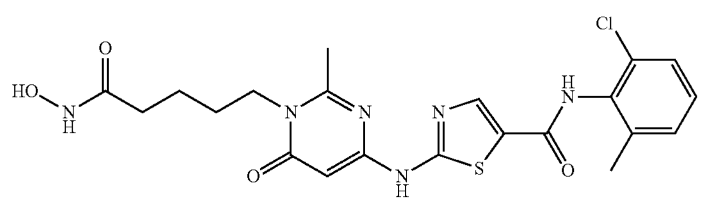 [SMILES: Cc1cccc(Cl)c1NC(=O)c1cnc(Nc2cc(=O)n(CCCCC(=O)NO)c(C)n2)s1] |
| 40 | 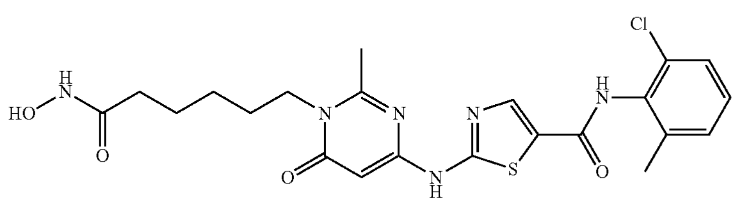 [SMILES: Cc1cccc(Cl)c1NC(=O)c1cnc(Nc2cc(=O)n(CCCCCC(=O)NO)c(C)n2)s1] |

TABLE A-continued

| Compound # | Structure |
|---|---|
| 41 | 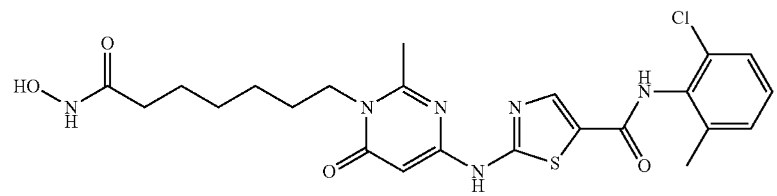 [SMILES: Cc1cccc(Cl)c1NC(=O)c1cnc(Nc2cc(=O)n(CCCCCCC(=O)NO)c(C)n2)s1] |
| 42 | 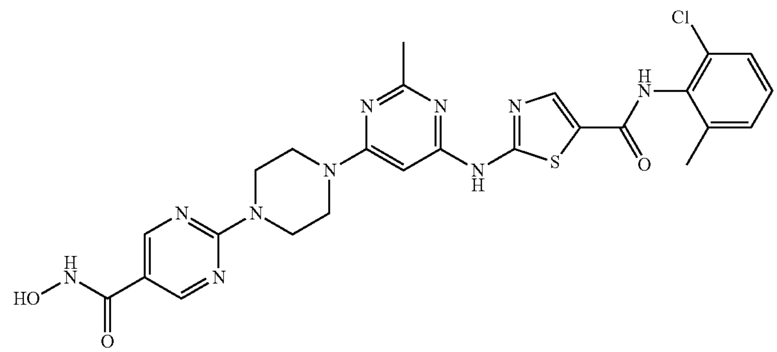 [SMILES: Cc1nc(Nc2ncc(C(=O)Nc3c(C)cccc3Cl)s2)cc(N2CCN(c3ncc(C(=O)NO)cn3)CC2)n1] |
| 43 | 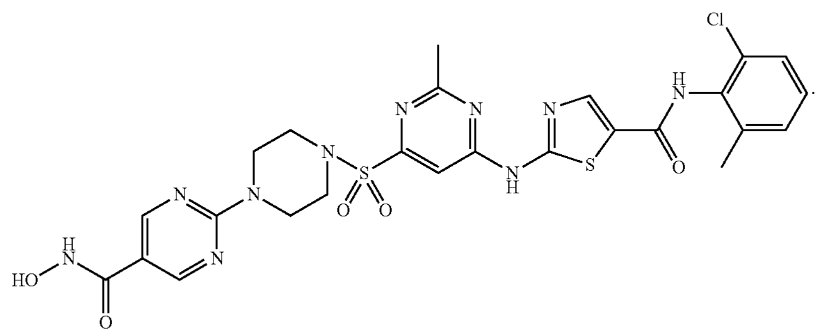 [SMILES: Cc1nc(Nc2ncc(C(=O)Nc3c(C)cccc3Cl)s2)cc(S(=O)(=O)N2CCN(c3ncc(C(=O)NO)cn3)CC2)n1 ; "."] |

9. The method of claim 1, wherein the compound represented by Formula I is

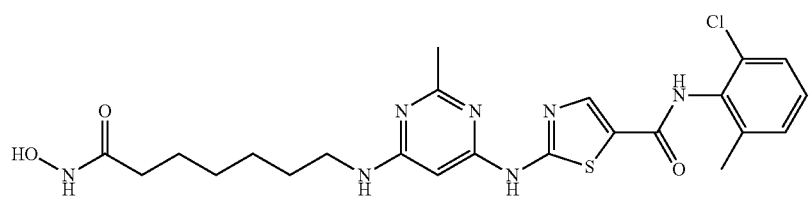 [SMILES: Cc1nc(NCCCCCCC(=O)NO)cc(Nc2ncc(C(=O)Nc3c(C)cccc3Cl)s2)n1]

or a pharmaceutically acceptable salt thereof.

10. The method of claim 1, wherein the cancer is leukemia, lymphoma or a solid tumor.

11. The method of claim 1, wherein the cancer is selected from the group consisting of cutaneous T-cell lymphoma, noncutaneous peripheral T-cell lymphoma, chronic myelogenous leukemia, acute myelogenous leukemia, non-Hodgkin lymphoma, acute lymphatic leukemia, chronic lymphatic leukemia, hepatocellular carcinoma, head and neck cancers, renal cancer, ovarian cancer, lung cancer, breast cancer, pancreatic cancer, and stomach cancer.

12. The method of claim 7, wherein the cancer is leukemia, lymphoma or a solid tumor.

13. The method of claim 7, wherein the cancer is selected from the group consisting of cutaneous T-cell lymphoma, noncutaneous peripheral T-cell lymphoma, chronic myelogenous leukemia, acute myelogenous leukemia, non-Hodgkin lymphoma, acute lymphatic leukemia, chronic lymphatic leukemia, hepatocellular carcinoma, head and neck cancers, renal cancer, ovarian cancer, lung cancer, breast cancer, pancreatic cancer, and stomach cancer.

14. The method of claim 9, wherein the cancer is leukemia, lymphoma or a solid tumor.

15. The method of claim 9, wherein the cancer is selected from the group consisting of cutaneous T-cell lymphoma, noncutaneous peripheral T-cell lymphoma, chronic myelogenous leukemia, acute myelogenous leukemia, non-Hodgkin lymphoma, acute lymphatic leukemia, chronic lymphatic leukemia, hepatocellular carcinoma, head and neck cancers, renal cancer, ovarian cancer, lung cancer, breast cancer, pancreatic cancer, and stomach cancer.

* * * * *

UNITED STATES PATENT AND TRADEMARK OFFICE
CERTIFICATE OF CORRECTION

PATENT NO. : 8,426,419 B2  
APPLICATION NO. : 13/010542  
DATED : April 23, 2013  
INVENTOR(S) : Xiong Cai et al.

Page 1 of 1

It is certified that error appears in the above-identified patent and that said Letters Patent is hereby corrected as shown below:

In the Claims:

Column 69  
Claim 6, line 1, after "compound of" insert --Formula I--.

Column 70  
Claim 7: line 18, after "Src," replace "Ber-Abl" with --Bcr-Abl--;  
line 34, replace "$C_1C_6$ alkyl" with --$C_1$-$C_6$ alkyl--;  
line 35, after "alkenyl, $C_2$-$C_6$" insert --alkynyl--;  
line 40, replace "$C_1C_6$" with --$C_1$-$C_8$--;  
line 41, replace "$C_2$-$C_6$ alkenyl, $C_2$-$C_6$ alkynyl" with --$C_2$-$C_8$ alkenyl, $C_2$-$C_8$ alkynyl--.

Signed and Sealed this  
Second Day of July, 2013

Teresa Stanek Rea  
*Acting Director of the United States Patent and Trademark Office*